(12) United States Patent
Page et al.

(10) Patent No.: US 8,940,732 B2
(45) Date of Patent: Jan. 27, 2015

(54) DIAGNOSIS OF AUTISM SPECTRUM DISORDERS AND ITS TREATMENT WITH AN ANTAGONIST OR INHIBITOR OF THE 5-HT2C RECEPTOR SIGNALING PATHWAY

(75) Inventors: Damon Theron Page, Arlington, MA (US); Mriganka Sur, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 344 days.

(21) Appl. No.: 12/688,171

(22) Filed: Jan. 15, 2010

(65) Prior Publication Data

US 2010/0298304 A1 Nov. 25, 2010

Related U.S. Application Data

(60) Provisional application No. 61/145,294, filed on Jan. 16, 2009.

(51) Int. Cl.
| | |
|---|---|
| *A61K 31/551* | (2006.01) |
| *A61K 31/4045* | (2006.01) |
| *A61K 31/472* | (2006.01) |
| *A61P 25/28* | (2006.01) |
| *C12Q 1/68* | (2006.01) |
| *A61K 31/403* | (2006.01) |

(Continued)

(52) U.S. Cl.
CPC ............ *C12Q 1/6883* (2013.01); *A61K 31/403* (2013.01); *A61K 31/435* (2013.01); *A61K 31/444* (2013.01); *A61K 31/5513* (2013.01); *C12N 15/1136* (2013.01); *C12N 15/1138* (2013.01); *C12N 2310/14* (2013.01); *C12Q 2600/156* (2013.01)

USPC ........... 514/220; 514/291; 514/307; 514/333; 514/418; 435/6.16

(58) Field of Classification Search
CPC . A61K 31/403; A61K 31/435; A61K 31/444; A61K 31/5513; C12N 15/1136; C12N 15/1138; C12N 2310/14; C12Q 1/6883; C12Q 2600/156
USPC .......... 514/220, 291, 307, 333, 418; 435/6.16
See application file for complete search history.

(56) References Cited

U.S. PATENT DOCUMENTS

| | | | |
|---|---|---|---|
| 4,816,567 | A | 3/1989 | Cabilly et al. |
| 5,225,539 | A | 7/1993 | Winter |

(Continued)

FOREIGN PATENT DOCUMENTS

| | | |
|---|---|---|
| EP | 1 782 813 A1 | 5/2007 |
| WO | WO 96/23783 A1 | 8/1996 |

(Continued)

OTHER PUBLICATIONS

Cook et al. (J. Am. Acad. Child Adolesc. Psychiatry, vol. 31: 4, 1992, pp. 739-745.*

(Continued)

*Primary Examiner* — Savitha Rao
(74) *Attorney, Agent, or Firm* — Wolf, Greenfield & Sacks, P.C.

(57) ABSTRACT

The invention relates to methods for diagnosis and treatment of autism spectrum disorders, particularly for autism spectrum disorders characterized by increased head size (circumference) and deficits in social behavior.

11 Claims, 8 Drawing Sheets

(51) Int. Cl.
*A61K 31/435* (2006.01)
*A61K 31/444* (2006.01)
*A61K 31/5513* (2006.01)
*C12N 15/113* (2010.01)

(56) References Cited

U.S. PATENT DOCUMENTS

| | | | |
|---|---|---|---|
| 5,585,089 | A | 12/1996 | Queen et al. |
| 5,693,762 | A | 12/1997 | Queen et al. |
| 5,859,205 | A | 1/1999 | Adair et al. |
| 2006/0194201 | A1 | 8/2006 | Fryns et al. |
| 2007/0003922 | A1 | 1/2007 | Amaral et al. |
| 2007/0299096 | A1 | 12/2007 | Silva |
| 2008/0293706 | A1 | 11/2008 | Feng et al. |
| 2008/0306057 | A1 | 12/2008 | Palmer et al. |

FOREIGN PATENT DOCUMENTS

| | | |
|---|---|---|
| WO | WO 97/48699 A1 | 12/1997 |
| WO | WO 97/48700 A1 | 12/1997 |
| WO | WO 02/14273 A1 | 2/2002 |
| WO | WO 2006/113837 A2 | 10/2006 |
| WO | WO 2008/027013 A2 | 3/2008 |
| WO | WO 2008/153929 A1 | 12/2008 |

OTHER PUBLICATIONS

Ni et al. (Proc. Natl. Acad. Sci. USA, vol. 94. pp. 2036-2040, 1997).*
Cook et al.1996 (Current opinion in pediatrics, 1996, vol. 8, pp. 348-354.*
DSM criteria document (dated 2007, downloaded from the internet on Nov. 14, 2011, URL: http://www.unstrange.com/dsm1.html.*
Kennett et al. (Neuropharmacology, vol. 36 (4/5) 1997, pp. 609-620).*
Akagami et al., PPAR agonist, pioglitazone inhibits interleukin-18 (IL-18)-induced gene expression and apoptosis in cardiac myocytes. Journal of Cardiac Failure. 2006;12(8):S162-3, Section 1010.
Bagdy et al., Anxiety-like effects induced by acute fluoxetine, sertraline or m-CPP treatment are reversed by pretreatment with the 5-HT2C receptor antagonist SB-242084 but not the 5-HT1A receptor antagonist WAY-100635. Int J Neuropsychopharmacol. Dec. 2001;4(4):399-408.
Beaulieu et al., Role of GSK3 beta in behavioral abnormalities induced by serotonin deficiency. Proc Natl Acad Sci U S A. Jan. 29, 2008;105(4):1333-8. Epub Jan. 22, 2008.
Bengel et al., Altered brain serotonin homeostasis and locomotor insensitivity to 3, 4-methylenedioxymethamphetamine ("Ecstasy") in serotonin transporter-deficient mice. Mol Pharmacol. Apr. 1998;53(4):649-55.
Boris et al., Effect of pioglitazone treatment on behavioral symptoms in autistic children. J Neuroinflammation. Jan. 5, 2007;4:3.
Brune et al., 5-HTTLPR Genotype-Specific Phenotype in Children and Adolescents With Autism. Am J Psychiatry. Dec. 2006;163(12):2148-56.
Butler et al., Subset of individuals with autism spectrum disorders and extreme macrocephaly associated with germline PTEN tumour suppressor gene mutations. J Med Genet. Apr. 2005;42(4):318-21.
Chang et al., Phosphatase PTEN in neuronal injury and brain disorders. Trends Neurosci. Nov. 2007;30(11):581-6. Epub Oct. 23, 2007.
Courchesne et al., Evidence of brain overgrowth in the first year of life in autism. JAMA. Jul. 16, 2003;290(3):337-44.
Cowen et al., 5-HT receptors couple to activation of Akt, but not extracellular-regulated kinase (ERK), in cultured hippocampal neurons. J Neurochem. May 2005;93(4):910-7.
Cowen, Serotonin and neuronal growth factors—a convergence of signaling pathways. J Neurochem. Jun. 2007;101(5):1161-71. Epub Jan. 5, 2007.
De Paula et al., Hydrophobization and bioconjugation for enhanced siRNA delivery and targeting. RNA. Apr. 2007;13(4):431-56. Epub Feb. 28, 2007.

Dekeyne et al., S32006, a novel 5-HT2C receptor antagonist displaying broad-based antidepressant and anxiolytic properties in rodent models. Psychopharmacology (Berl). Sep. 2008;199(4):549-68. Epub Jun. 4, 2008.
Ferguson et al., Oxytocin in the medial amygdala is essential for social recognition in the mouse. J Neurosci. Oct. 15, 2001;21(20):8278-85.
Frankland et al., Sensorimotor gating abnormalities in young males with fragile X syndrome and Fmr1-knockout mice. Mol Psychiatry. Apr. 2004;9(4):417-25.
Garcia-Colunga et al., Blockage of muscle and neuronal nicotinic acetylcholine receptors by fluoxetine (Prozac). Proc Natl Acad Sci U S A. Mar. 4, 1997;94(5):2041-4.
Gaspar et al., The developmental role of serotonin: news from mouse molecular genetics. Nat Rev Neurosci. Dec. 2003;4(12):1002-12.
Hessl et al., Brief report: aggression and stereotypic behavior in males with fragile X syndrome—moderating secondary genes in a "single gene" disorder. J Autism Dev Disord. Jan. 2008;38(1):184-9. Epub Mar. 6, 2007.
Hsu et al., Activation of Akt1 by human 5-hydroxytryptamine (serotonin)1B receptors is sensitive to inhibitors of MEK. J Pharmacol Exp Ther. Aug. 2001;298(2):825-32.
Ihle et al., The phosphatidylinositol-3-kinase inhibitor PX-866 overcomes resistance to the epidermal growth factor receptor inhibitor gefitinib in A-549 human non-small cell lung cancer xenografts. Mol Cancer Ther. Sep. 2005;4(9):1349-57.
Iwase et al., Synthesis and properties of modified siRNA having amide-linked oligoribonucleosides at their 3' overhang regions. Nucleic Acids Symp Ser (Oxf). 2006;(50):175-6.
Jiang et al., Both the establishment and the maintenance of neuronal polarity require active mechanisms: critical roles of GSK-3beta and its upstream regulators. Cell. Jan. 14, 2005;120(1):123-35.
Kenet et al., Perinatal exposure to a noncoplanar polychlorinated biphenyl alters tonotopy, receptive fields, and plasticity in rat primary auditory cortex. Proc Natl Acad Sci U S A. May 1, 2007;104(18):7646-51. Epub Apr. 25, 2007.
Kwon et al., Pten regulates neuronal arborization and social interaction in mice. Neuron. May 4, 2006;50(3):377-88.
Langer, New methods of drug delivery. Science. Sep. 28, 1990;249(4976):1527-33.
Li et al., In vivo regulation of glycogen synthase kinase-3beta (GSK3beta) by serotonergic activity in mouse brain. Neuropsychopharmacology. Aug. 2004;29(8):1426-31.
Lim et al., The role of caveolin-1 in PCB77-induced eNOS phosphorylation in human-derived endothelial cells. Am J Physiol Heart Circ Physiol. Dec. 2007;293(6):H3340-7. Epub Oct. 12, 2007.
McAlonan et al., Brain anatomy and sensorimotor gating in Asperger's syndrome. Brain. Jul. 2002;125(Pt 7):1594-606.
McCracken et al., Risperidone in children with autism and serious behavioral problems. N Engl J Med. Aug. 1, 2002;347(5):314-21.
McManus et al., Gene silencing using micro-RNA designed hairpins. RNA. Jun. 2002;8(6):842-50.
Muhle et al., The genetics of autism. Pediatrics. May 2004;113(5):e472-86.
Nadler et al., Automated apparatus for quantitation of social approach behaviors in mice. Genes Brain Behav. Oct. 2004;3(5):303-14.
Paddison et al., Short hairpin RNAs (shRNAs) induce sequence-specific silencing in mammalian cells. Genes Dev. Apr. 15, 2002;16(8):948-58.
Page et al., Haploinsufficiency for Pten and Serotonin transporter cooperatively influences brain size and social behavior. Proc Natl Acad Sci U S A. Feb. 10, 2009;106(6):1989-94.
Patel et al., Tumor suppressor and anti-inflammatory actions of PPARgamma agonists are mediated via upregulation of PTEN. Curr Biol. May 15, 2001;11(10):764-8.
Podsypanina et al., Mutation of Pten/Mmac1 in mice causes neoplasia in multiple organ systems. Proc Natl Acad Sci U S A. Feb. 16, 1999;96(4):1563-8.
Ravikumar et al., Inhibition of mTOR induces autophagy and reduces toxicity of polyglutamine expansions in fly and mouse models of Huntington disease. Nat Genet. Jun. 2004;36(6):585-95 Epub May 16, 2004.

(56) References Cited

OTHER PUBLICATIONS

Raymond et al., Safety and pharmacokinetics of escalated doses of weekly intravenous infusion of CCI-779, a novel mTOR inhibitor, in patients with cancer. J Clin Oncol. Jun. 15, 2004;22(12):2336-47. Epub May 10, 2004.
Rubenstein et al., Model of autism: increased ratio of excitation/inhibition in key neural systems. Genes Brain Behav. Oct. 2003;2(5):255-67.
Salichon et al., Excessive activation of serotonin (5-HT) 1B receptors disrupts the formation of sensory maps in monoamine oxidase a and 5-ht transporter knock-out mice. J Neurosci. Feb. 1, 2001;21(3):884-96.
Shen et al., Essential role for nuclear PTEN in maintaining chromosomal integrity. Cell. Jan. 12, 2007;128(1):157-70.
Sweeten et al., Increased prevalence of familial autoimmunity in probands with pervasive developmental disorders. Pediatrics. Nov. 2003;112(5):e420.
Teresi et al., Increased PTEN expression due to transcriptional activation of PPARgamma by Lovastatin and Rosiglitazone. Int J Cancer. May 15, 2006;118(10):2390-8.
Yang et al., Akt/protein kinase B signaling inhibitor-2, a selective small molecule inhibitor of Akt signaling with antitumor activity in cancer cells overexpressing Akt. Cancer Res. Jul. 1, 2004;64(13):4394-9.
Yu et al., RNA interference by expression of short-interfering RNAs and hairpin RNAs in mammalian cells. Proc Natl Acad Sci U S A. Apr. 30, 2002;99(9):6047-52. Epub Apr. 23, 2002.
Backman et al., Deletion of Pten in mouse brain causes seizures, ataxia and defects in soma size resembling Lhermitte-Duclos disease. Nat Genet. Dec. 2001;29(4):396-403. Epub Nov. 19, 2001.
Bartlett et al., Three autism candidate genes: a synthesis of human genetic analysis with other disciplines. Int J Dev Neurosci. Apr.-May 2005;23(2-3):221-34.
Bonanno et al., Pharmacological characterization of release-regulating serotonin autoreceptors in rat cerebellum. Eur J Pharmacol. Jul. 31, 1986;126(3):317-21.
Bonhaus et al., RS-102221: a novel high affinity and selective, 5-HT2C receptor antagonist. Neuropharmacology. Apr.-May 1997;36(4-5):621-9.
Bonnin et al., Expression mapping of 5-HT1 serotonin receptor subtypes during fetal and early postnatal mouse forebrain development. Neuroscience. Aug. 25, 2006;141(2):781-94. Epub Jul. 7, 2006.
Bonnin et al., Serotonin modulates the response of embryonic thalamocortical axons to netrin-1. Nat Neurosci. May 2007;10(5):588-97. Epub Apr. 22, 2007.
Brodkin et al., Social approach-avoidance behavior of inbred mouse strains towards DBA/2 mice. Brain Res. Mar. 26, 2004;1002(1-2):151-7.
Bromidge et al., 1-[2-[(Heteroarylmethoxy)aryl]carbamoyl]indolines are selective and orally active 5-HT2C receptor inverse agonists. Bioorg Med Chem Lett. Aug. 21, 2000;10(16):1867-70.
Bromidge et al., 6-Chloro-5-methy1-1-[[2-[(2-methyl-3-pyridyl)oxy]-5-pyridyl]carbamoyl]-indoline (SB-242084): the first selective and brain penetrant 5-HT2C receptor antagonist. J Med Chem. Oct. 24, 1997;40(22):3494-6.
Cabanlit et al., Brain-specific autoantibodies in the plasma of subjects with autistic spectrum disorder. Ann N Y Acad Sci. Jun. 2007;1107:92-103.
Choung et al., Chemical modification of siRNAs to improve serum stability without loss of efficacy. Biochem Biophys Res Commun. Apr. 14, 2006;342(3):919-27. Epub Feb. 20, 2006.
Courchesne et al., Brain overgrowth in autism during a critical time in development: implications for frontal pyramidal neuron and interneuron development and connectivity. Int J Dev Neurosci. Apr.-May 2005;23(2-3):153-70.
Courchesne et al., Why the frontal cortex in autism might be talking only to itself: local over-connectivity but long-distance disconnection. Curr Opin Neurobiol. Apr. 2005;15(2):225-30. Epub Mar. 12, 2005.
Covey et al., Akt activation by arachidonic acid metabolism occurs via oxidation and inactivation of PTEN tumor suppressor. Oncogene. Aug. 23, 2007;26(39):5784-92. Epub Mar. 19, 2007.
Crawley, Designing mouse behavioral tasks relevant to autistic-like behaviors. Ment Retard Dev Disabil Res Rev. Nov. 2004;10(4):248-58.
Crawley et al., Social approach behaviors in oxytocin knockout mice: comparison of two independent lines tested in different laboratory environments. Neuropeptides. Jun. 2007;41(3):145-63. Epub Apr. 8, 2007.
Cully et al., Beyond PTEN mutations: the PI3K pathway as an integrator of multiple inputs during tumorigenesis. Nat Rev Cancer. Mar. 2006;6(3):184-92. Epub Feb. 2, 2006.
Di Cristofano et al., Impaired Fas response and autoimmunity in Pten+/− mice. Science. Sep. 24, 1999;285(5436):2122-5.
Di Matteo et al., SB 242084: A selective 5-HT$_{2C}$ receptor antagonist. CNS Drug Rev. Dec. 31, 2000;6(3):195-205.
Dunbar et al., Evolution in the social brain. Science. Sep. 7, 2007;317(5843):1344-7.
Eng, PTEN: one gene, many syndromes. Hum Mutat. Sep. 2003;22(3):183-98.
Ferguson et al., Social amnesia in mice lacking the oxytocin gene. Nat Genet. Jul. 2000;25(3):284-8.
Ferrari et al., Characterization of antisense oligonucleotides comprising 2'-deoxy-2'-fluoro-beta-D-arabinonucleic acid (FANA): specificity, potency, and duration of activity. Ann N Y Acad Sci. Oct. 2006;1082:91-102.
Goffin et al., PTEN mutation in a family with Cowden syndrome and autism. Am J Med Genet. Aug. 8, 2001;105(6):521-4.
Hamprecht et al., 5-HT2C antagonists based on fused heterotricyclic templates: design, synthesis and biological evaluation. Bioorg Med Chem Lett. Jan. 15, 2007;17(2):424-7. Epub Oct. 17, 2006.
Hamprecht et al., Isoindolone derivatives, a new class of 5-HT2C antagonists: synthesis and biological evaluation. Bioorg Med Chem Lett. Jan. 15, 2007;17(2):428-33. Epub Oct. 17, 2006.
Harada et al., Anxiolytic activity of a novel potent serotonin 5-HT2C receptor antagonist FR260010: a comparison with diazepam and buspirone. Eur J Pharmacol. Dec. 28, 2006;553(1-3):171-84. Epub Sep. 28, 2006.
Herman et al., Genetic testing in autism: how much is enough? Genet Med. May 2007;9(5):268-74.
Herman et al., Increasing knowledge of PTEN germline mutations: Two additional patients with autism and macrocephaly. Am J Med Genet A. Mar. 15, 2007;143(6):589-93.
Ji et al., Disruption of PTEN coupling with 5-HT2C receptors suppresses behavioral responses induced by drugs of abuse. Nat Med. Mar. 2006;12(3):324-9. Epub Feb. 12, 2006.
Kwon et al., Pten regulates neuronal soma size: a mouse model of Lhermitte-Duclos disease. Nat Genet. Dec. 2001;29(4):404-11. Epub Nov. 19, 2001.
Lindsley et al., The PI3K/Akt pathway: recent progress in the development of ATP-competitive and allosteric Akt kinase inhibitors. Curr Cancer Drug Targets. Feb. 2008;8(1):7-18.
Lôo et al., Determination of the dose of agomelatine, a melatoninergic agonist and selective 5-HT(2C) antagonist, in the treatment of major depressive disorder: a placebo-controlled dose range study. Int Clin Psychopharmacol. Sep. 2002;17(5):239-47.
Luo et al., Impaired olfactory behavior in mice deficient in the alpha subunit of G(o). Brain Res. Jun. 21, 2002;941(1-2):62-71.
Malone et al., Olanzapine versus haloperidol in children with autistic disorder: an open pilot study. J Am Acad Child Adolesc Psychiatry. Aug. 2001;40(8):887-94.
Martin et al., Influence of the 5-HT2C receptor antagonist, SB-242084, in tests of anxiety. Pharmacol Biochem Behav. Apr. 2002;71(4):615-25.
Marui et al., Association between the neurofibromatosis-1 (NF1) locus and autism in the Japanese population. Am J Med Genet B Neuropsychiatr Genet. Nov. 15, 2004;131B(1):43-7.
Mbarek et al., Association study of the NF1 gene and autistic disorder. Am J Med Genet. Dec. 15, 1999;88(6):729-32.
McCaffrey et al., RNA interference in adult mice. Nature. Jul. 4, 2002;418(6893):38-9.

(56) References Cited

OTHER PUBLICATIONS

Perry et al., Sensorimotor gating deficits in adults with autism. Biol Psychiatry. Feb. 15, 2007;61(4):482-6. Epub Feb. 7, 2006.

Puc et al., PTEN loss inhibits CHK1 to cause double stranded-DNA breaks in cells. Cell Cycle. Jul. 2005;4(7):927-9. Epub Jul. 3, 2005.

Sacco et al., Clinical, morphological, and biochemical correlates of head circumference in autism. Biol Psychiatry. Nov. 1, 2007;62(9):1038-47. Epub Jul. 20, 2007.

Sainio et al., Antisense inhibition of low-affinity nerve growth factor receptor in kidney cultures: power and pitfalls. Cell Mol Neurobiol. Oct. 1994;14(5):439-57.

Sebat et al., Strong association of de novo copy number mutations with autism. Science. Apr. 20, 2007;316(5823):445-9. Epub Mar. 15, 2007.

Vargas et al., Neuroglial activation and neuroinflammation in the brain of patients with autism. Ann Neurol. Jan. 2005;57(1):67-81. Epub Nov. 15, 2004.

Wagner et al., Potent and selective inhibition of gene expression by an antisense heptanucleotide. Nat Biotechnol. Jul. 1996;14(7):840-4.

Wassink et al., Cerebral cortical gray matter overgrowth and functional variation of the serotonin transporter gene in autism. Arch Gen Psychiatry. Jun. 2007;64(6):709-17.

Wood et al., SB-243213; a selective 5-HT2C receptor inverse agonist with improved anxiolytic profile: lack of tolerance and withdrawal anxiety. Neuropharmacology. Aug. 2001;41(2):186-99.

Xia et al., Gene silencing activity of siRNAs with a ribo-difluorotoluyl nucleotide. ACS Chem Biol. Apr. 25, 2006;1(3):176-83. Epub Apr. 17, 2006.

Zhang et al., PPARgamma activator rosiglitazone inhibits cell migration via upregulation of PTEN in human hepatocarcinoma cell line BEL-7404. Cancer Biol Ther. Aug. 2006;5(8):1008-14. Epub Aug. 7, 2006.

Zhu et al., Isoquinoline-pyridine-based protein kinase B/Akt antagonists: SAR and in vivo antitumor activity. Bioorg Med Chem Lett. Jun. 15, 2006;16(12):3150-5. Epub Apr. 5, 2006.

\* cited by examiner

US 8,940,732 B2

DIAGNOSIS OF AUTISM SPECTRUM DISORDERS AND ITS TREATMENT WITH AN ANTAGONIST OR INHIBITOR OF THE 5-HT2C RECEPTOR SIGNALING PATHWAY

RELATED APPLICATION

This application claims the benefit under 35 U.S.C. §119(e) of U.S. provisional application Ser. No. 61/145,294, filed Jan. 16, 2009, the disclosure of which is incorporated by reference herein in its entirety.

FIELD OF THE INVENTION

The invention relates to methods for diagnosis and treatment of autism spectrum disorders, particularly for autism spectrum disorders characterized by increased head size (circumference) and deficits in social behavior.

BACKGROUND OF THE INVENTION

Autism spectrum disorder (ASD) is highly heritable, with a 2-3% recurrence rate in siblings and a 60-90% concordance rate in monozygotic twins. However, known genetic causes—for example, single gene disorders such as Fragile-X or tuberous sclerosis, or chromosomal abnormalities—account for approximately 10% of ASD cases. Thus, the majority of cases of ASD are of unknown cause at present. Current estimates are that ASD susceptibility is conferred by numerous genes interacting with one another, as well as with environmental factors.

SUMMARY OF THE INVENTION

Based on experiments conducted with mice heterozygous for PTEN and/or SLC6A4, the applicants have determined that these genes and their expression products are biomarkers for autism spectrum disorders. Based on the biochemical interactions of the expression products of PTEN and/or SLC6A4, the applicants have determined that antagonists or inhibitors of the 5-HT2c receptor signaling pathway unexpectedly are viable candidates for human ASD therapeutics.

Biomarkers for autism spectrum disorders (ASD) are provided, particularly for ASD characterized by increased head size (circumference) and deficits in social behavior. The biomarkers are genetic or epigenetic variations that result in decreased expression or function of PTEN (PTEN deficiency) and/or genetic or epigenetic variations that result in decreased expression or function of SLC6A4 (SLC6A4 deficiency). Examples of epigenetic variations that one could use as biomarkers include inflammation, which results in up-regulation of TGF-beta, which acts to suppress PTEN transcription, and exposure to arachidonic acid, which suppresses PTEN (see Covey et al., Oncogene. 26(39):578457-92, 2007). An additional biomarker for ASD is elevated circulating serotonin levels.

Methods for treating ASD also are provided. In some embodiments, the treatment methods include reducing the availability of brain serotonin. In specific embodiments, agonists of SLC6A4 are used to reduce the availability of brain serotonin. In other embodiments, the treatment methods include reducing the activation of the PI3 Kinase pathway or inhibiting the serotonin receptor type 5-HT2c pathway. In specific embodiments, the ASD is marked by one or more of: PTEN deficiency, SLC6A4 deficiency, increase in head size (circumference), increased circulating serotonin.

According to one aspect of the invention, methodS for treating an autism spectrum disorder are provided. The methods include administering to a subject in need of such treatment one or more therapeutic molecules that is an antagonist or inhibitor of the 5-HT2c receptor signaling pathway. In some embodiments, the antagonist or inhibitor of the 5-HT2c receptor signaling pathway is (1) an antagonist or inhibitor of 5-HT2c receptor, phosphoinositol-3 kinase (PI3K), Akt, mTOR, Creb and/or NF-kappa B, and/or (2) an agonist of activator of GSK-3beta, in an amount effective to treat the subject.

In some embodiments, an antagonist or inhibitor of 5-HT2c receptor is administered, preferably an antagonist or inhibitor that can pass the into the brain. In certain embodiments the antagonist or inhibitor of 5-HT2c receptor is SB242084. In some embodiments, the dose of SB 242084 administered is about 0.1-1 mg/kg/day. In other embodiments, the dose of SB 242084 administered is about 1-10 mg/kg/day. In still other embodiments, the SB 242084 is administered intermittently at a dose of about 0.1-10 mg/kg.

In some embodiments, the antagonist or inhibitor of the 5-HT2c receptor signaling pathway is not marketed (as of the filing date of this application) as an atypical antipsychotic medication, a selective serotonin reuptake inhibitors (SSRI) or a PPAR-gamma agonist. In certain embodiments, the antagonist or inhibitor of 5-HT2c receptor signaling pathway is not risperidone, olanzapine, ziprasidone, fluoxetine, or a thiazolidinedione.

In some embodiments, an antagonist or inhibitor of PI3K is administered, preferably an antagonist or inhibitor that can pass the into the brain. In certain embodiments, the antagonist or inhibitor of PI3K is sunitinib (SUTENT®).

In some embodiments, an antagonist or inhibitor of Akt is administered, preferably an antagonist or inhibitor that can pass the into the brain. In certain embodiments, the antagonist or inhibitor of Akt is clozapine or Nelfinavir (VIRACEPT).

In some embodiments, an antagonist or inhibitor of mTOR is administered, preferably an antagonist or inhibitor that can pass the into the brain. In certain embodiments, the antagonist or inhibitor of mTOR is rapamycin (sirolimus).

In some embodiments, the methods include administering an antagonist or inhibitor of Creb, an antagonist or inhibitor of NF-kappa B, or an agonist of activator of GSK-3beta, each of which preferably can pass the into the brain.

In some embodiments, the subject is a human.

In some embodiments, the antagonist or inhibitor of the 5-HT2c receptor signaling pathway is administered orally, intravenously, intramuscularly, intranasally, intraperitoneally, subcutaneously, or intrathecally.

In some embodiments, the antagonist or inhibitor of the 5-HT2c receptor signaling pathway is administered after diagnosis of the autism spectrum disorder.

In some embodiments, the antagonist or inhibitor of the 5-HT2c receptor signaling pathway is administered prophylactically before diagnosis of the autism spectrum disorder.

In some embodiments, the subject is free of symptoms otherwise calling for treatment with the antagonist or inhibitor of the 5-HT2c receptor signaling pathway.

In some embodiments, the methods also include testing the subject for PTEN deficiency and/or SLC6A4 deficiency and/or increased circulating serotonin. In certain embodiments, the antagonist or inhibitor of the 5-HT2c receptor signaling pathway is administered to the subject only if a PTEN deficiency and/or SLC6A4 deficiency and/or increased circulating serotonin is detected by the testing.

In some embodiments, the methods also include testing the subject for macrocephaly (brain overgrowth) and/or deficits in social behavior, such as a deficit in social interaction and/or a deficit in social memory. In certain embodiments, the antagonist or inhibitor of the 5-HT2c receptor signaling pathway is administered to the subject only if macrocephaly and/or deficits in social behavior are detected by the testing.

In some embodiments, the methods also include administering to the subject a second therapeutic for autism spectrum disorder, and wherein the second therapeutic and the antagonist or inhibitor of the 5-HT2c receptor signaling pathway are administered in a combined amount effective to treat the subject. In certain embodiments, the second therapeutic is risperidone, olanzapine, ziprasidone, fluoxetine or a PPAR-gamma agonist.

According to another aspect of the invention, methods for treating an autism spectrum disorder are provided. The methods include administering to a subject in need of such treatment an effective amount of one or more molecules that reduce expression of 5-HT2c receptor, phosphoinositol-3 kinase (PI3K), Akt, mTOR, Creb and/or NF-kappa B, and/or one or more molecules that increase expression of GSK-3beta, to treat the subject.

In some embodiments, the one or more molecules that reduce expression are one or more molecules that induce RNA interference. In certain embodiments, the one or more molecules that induce RNA interference are one or more short interfering nucleic acids (siNA). In some embodiments, the one or more siNA molecules are short interfering RNA (siRNA), double-stranded RNA (dsRNA), micro-RNA (miRNA), and short hairpin RNA (shRNA) molecules.

In some embodiments, the subject is a human.

In some embodiments, the one or more molecules that reduce expression and/or one or more molecules that increase expression is administered orally, intravenously, intramuscularly, intranasally, intraperitoneally, subcutaneously, or intrathecally.

In some embodiments, the one or more molecules that reduce expression and/or one or more molecules that increase expression is administered after diagnosis of the autism spectrum disorder.

In some embodiments, the one or more molecules that reduce expression and/or one or more molecules that increase expression is administered prophylactically before diagnosis of the autism spectrum disorder.

In some embodiments, the subject is free of symptoms otherwise calling for treatment with the one or more molecules that reduce expression and/or one or more molecules that increase expression.

In some embodiments, the methods also include testing the subject for PTEN deficiency and/or SLC6A4 deficiency and/or increased circulating serotonin. In certain embodiments, the one or more molecules that reduce expression and/or one or more molecules that increase expression is administered to the subject only if a PTEN deficiency and/or SLC6A4 deficiency and/or increased circulating serotonin is detected by the testing.

In some embodiments, the methods also include testing the subject for macrocephaly (brain overgrowth) and/or deficits in social behavior, such as a deficit in social interaction and/or a deficit in social memory. In certain embodiments, the one or more molecules that reduce expression and/or one or more molecules that increase expression is administered to the subject only if macrocephaly and/or deficits in social behavior are detected by the testing.

In some embodiments, the methods also include administering to the subject a second therapeutic for autism spectrum disorder. The second therapeutic and the one or more molecules that reduce expression and/or one or more molecules that increase expression are administered in a combined amount effective to treat the subject. In certain embodiments, the second therapeutic is an antagonist or inhibitor of the 5-HT2c receptor signaling pathway. In other embodiments, the second therapeutic is risperidone, olanzapine, ziprasidone, fluoxetine or a PPAR-gamma agonist.

According to another aspect of the invention, methods for diagnosing an autism spectrum disorder characterized by increased head size (circumference) and/or deficits in social behavior are provided. The methods include analyzing a biological sample from a subject for the presence of one or more biomarkers for autism spectrum disorders. The one or more biomarkers are, for example (1) the presence of one or more mutations or epigenetic variations in the Pten gene and/or the Slc6a4 gene, and/or (2) increased circulating serotonin levels relative to a normal range of circulating serotonin levels. The presence of the one or more biomarkers for autism spectrum disorders indicates that the subject has an autism spectrum disorder characterized by increased head size (circumference) and/or deficits in social behavior.

In some embodiments, the one or more mutations or epigenetic variations in the Pten gene and/or the Slc6a4 gene result in decreased expression or function of PTEN and/or decreased expression or function of SLC6A4.

In some embodiments, the methods also include preparing a report that indicates the status of the subject with respect to autism spectrum disorders.

In some embodiments, the methods include providing the analysis of the biological sample to a clinician administering health care to the subject.

In some embodiments, the deficit in social behavior is a deficit in social interaction and/or a deficit in social memory.

These and other aspects of the invention, as well as various advantages and utilities, will be more apparent with reference to the detailed description of the invention. Each aspect of the invention can encompass various embodiments as will be understood by the following description.

Figure 3A:
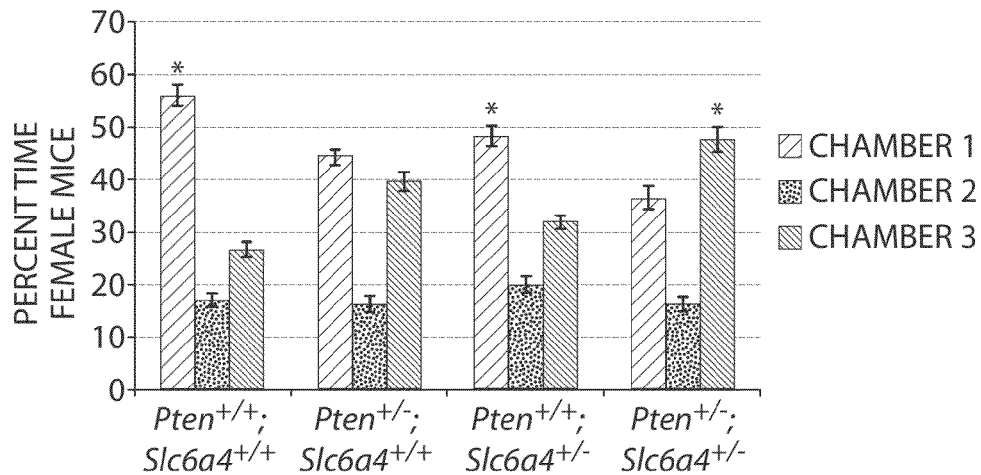
FIG. 3: Social behavior and prepulse inhibition in Pten and Slc6a4 haploinsufficient mice FIG. 3(A) Social approach data for 8 week old female Pten$^{+/+}$; Slc6a4$^{+/+}$ (n=13), Pten$^{+/-}$; Slc6a4$^{+/+}$ (n=13), Pten$^{+/+}$; Slc6a4$^{+/-}$ (n=11) and Pten$^{+/-}$; Slc6a4$^{+/-}$ (n=13) mice. * P<0.05, ANOVA within group comparison between chamber 1 and chamber 3. Error bars indicate SEM. In each group of bars, the order is: left bar=chamber 1, middle bar=chamber 2, right bar=chamber 3.
FIG. 3(B) Social approach data from panel (A) presented as approach-avoidance score for analysis across genotypes. Time spent with a social stimulus mouse in chamber 1 is significantly decreased in Pten$^{+/-}$; Slc6a4$^{+/-}$ mice as compared to Pten$^{+/+}$; Slc6a4$^{+/+}$, Pten$^{+/-}$; Slc6a4$^{+/+}$ and Pten$^{+/+}$; Slc6a4$^{+/-}$ mice ($F_{3,49}$=25.3; P<0.001). * P<0.05, ** P<0.01 (Tukey HSD test).
FIG. 3(C) Social approach and recognition data for 8 week old male mice. During trial 1, stimulus (located in chamber 1) and subject mouse interacted for 10 minutes. These were then separated for 30 minutes. Trial 2 then took place, during which the subject and stimulus mouse interacted for 5 minutes. Pten$^{+/+}$; Slc6a4$^{+/+}$ (n=12), Pten$^{+/-}$; Slc6a4$^{+/+}$ (n=10), Pten$^{+/+}$; Slc6a4$^{+/-}$ (n=8) and Pten$^{+/-}$; Slc6a4$^{+/-}$ (n=8) mice. * P<0.05, ANOVA within group comparison between chamber 1 and chamber 3. Error bars indicate SEM. In each group of bars, the order is: left bar=chamber 1, middle bar=chamber 2, right bar=chamber 3.
FIG. 3(D) Prepulse inhibition of the acoustic startle response in 8-week-old Pten$^{+/-}$; Slc6a4$^{+/-}$ mice. Pten$^{+/-}$; Slc6a4$^{+/+}$ and Pten$^{+/-}$; Slc6a4$^{+/-}$ mice have significant deficits in startle inhibition at a prepulse 16 db above background ($F_{3,46}$=3.6; P<0.05). * P <0.05 (Tukey HSD test). n=11 Pten$^{+/+}$; Slc6a4$^{+/+}$ (8 female), 10 Pten$^{+/-}$; Slc6a4$^{+/+}$ (7 female), 13 Pten$^{+/+}$; Slc6a4$^{+/-}$ (7 female) and 13 Pten$^{+/-}$; Slc6a4$^{+/-}$ (9 female) mice.
Figure 3B:
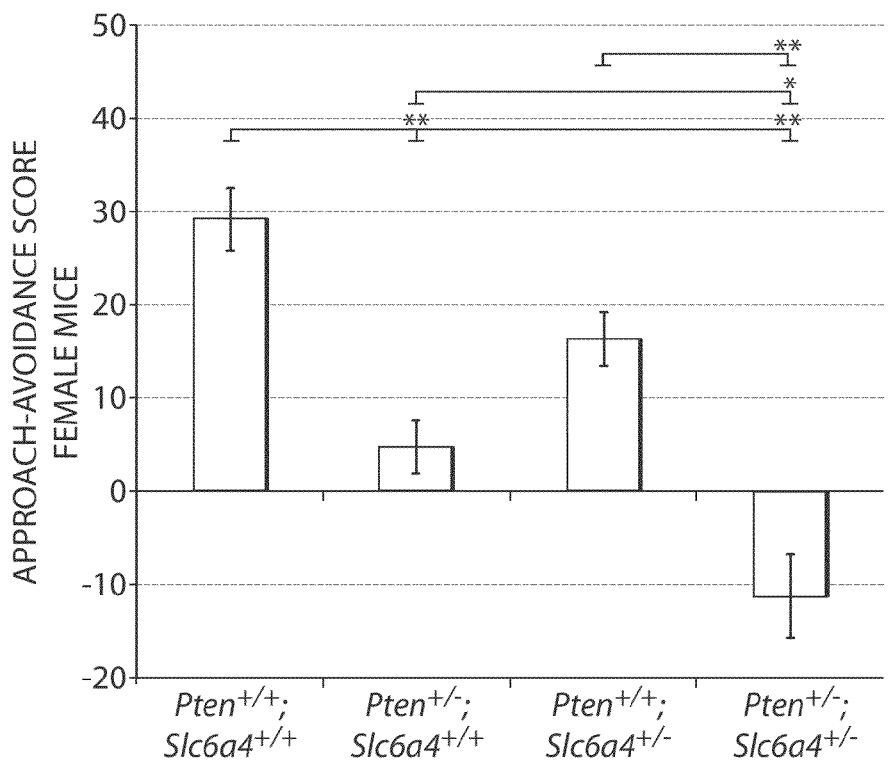

Group sizes are different than those reported in FIG. 3A-B because not all animals assayed for social approach were measured for brain mass.

Figure 5:
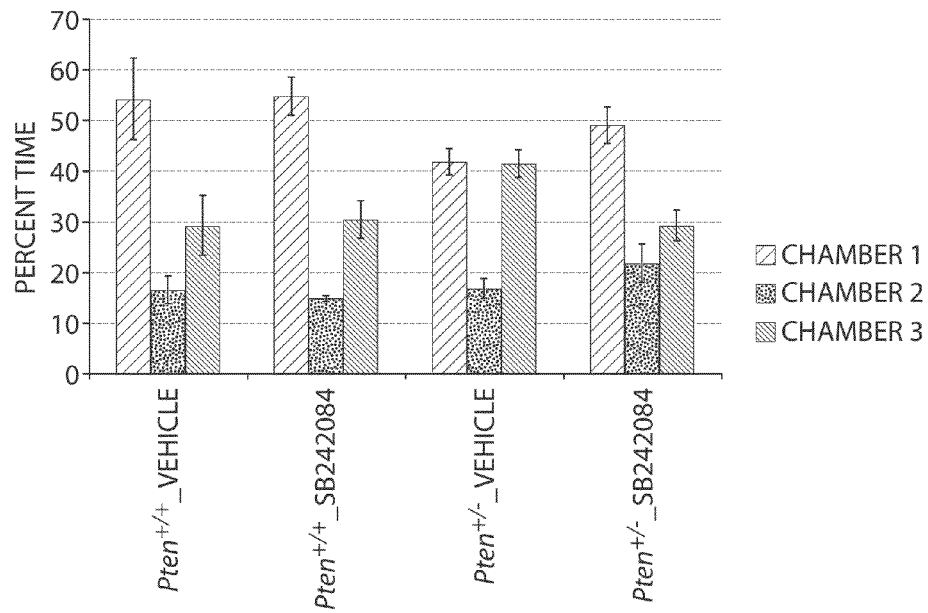

FIG. 5: Effects of the 5-HT2cR antagonist SB 242084 on social approach behavior in Pten haploinsufficient mice. The mice tested were female littermates, 8 weeks of age. The mice were given an IP injection of 0.3 mg/kg of SB 242084 or vehicle, 20 minutes prior to start of the assay. A social stimulus mouse was placed in chamber 1 and an identical empty cage was placed in chamber 3. The percent time the subject mouse spent interacting with the stimulus mouse was quantified over 10 minutes. Pten haploinsufficient mice treated with SB 242084 show a significant preference for interacting with the stimulus mouse, in contrast to vehicle treated mice of this genotype, which do not show this preference. For vehicle treated groups, n=6; for SB 242084-treated groups, n=8. * P<0.05, ANOVA within group comparison between chamber 1 and chamber 3. In each group of bars, the order is: left bar=chamber 1, middle bar=chamber 2, right bar=chamber 3.

Figure 6:
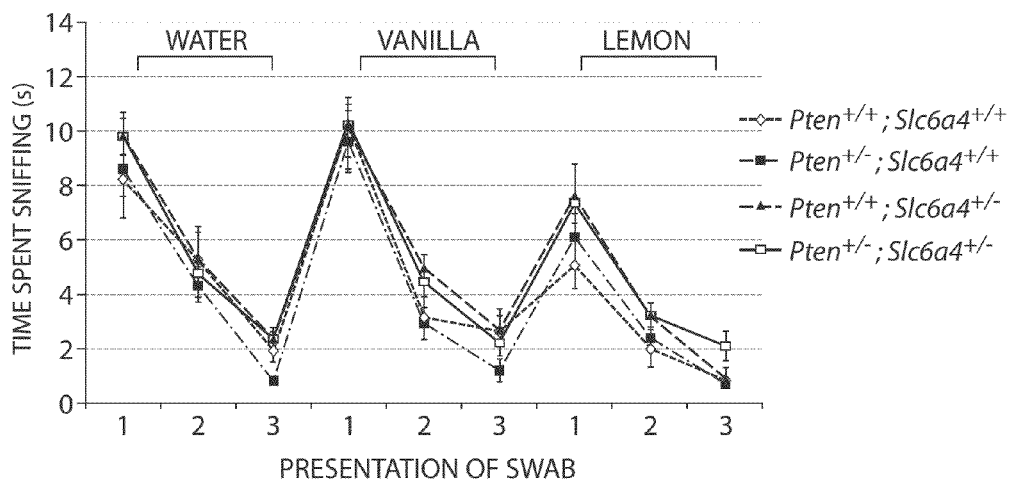

FIG. 6: Olfactory habituation/dishabituation assay for odor recognition and discrimination shows that the pattern of habituation and dishabituation to novel odors is unchanged in Pten and Slc6a4 haploinsufficient mice. Differences between genotypes for each time point are non-significant by ANOVA. Animals were tested at 6-9 weeks of age. n=10 Pten$^{+/+}$; Slc6a4$^{+/+}$ (8 female), 10 Pten$^{+/-}$; Slc6a4$^{+/+}$ (8 female), 9 Pten$^{+/+}$; Slc6a4$^{+/-}$ (4 female), 9 Pten$^{+/-}$; Slc6a4$^{+/-}$ (4 female).

Figure 7:
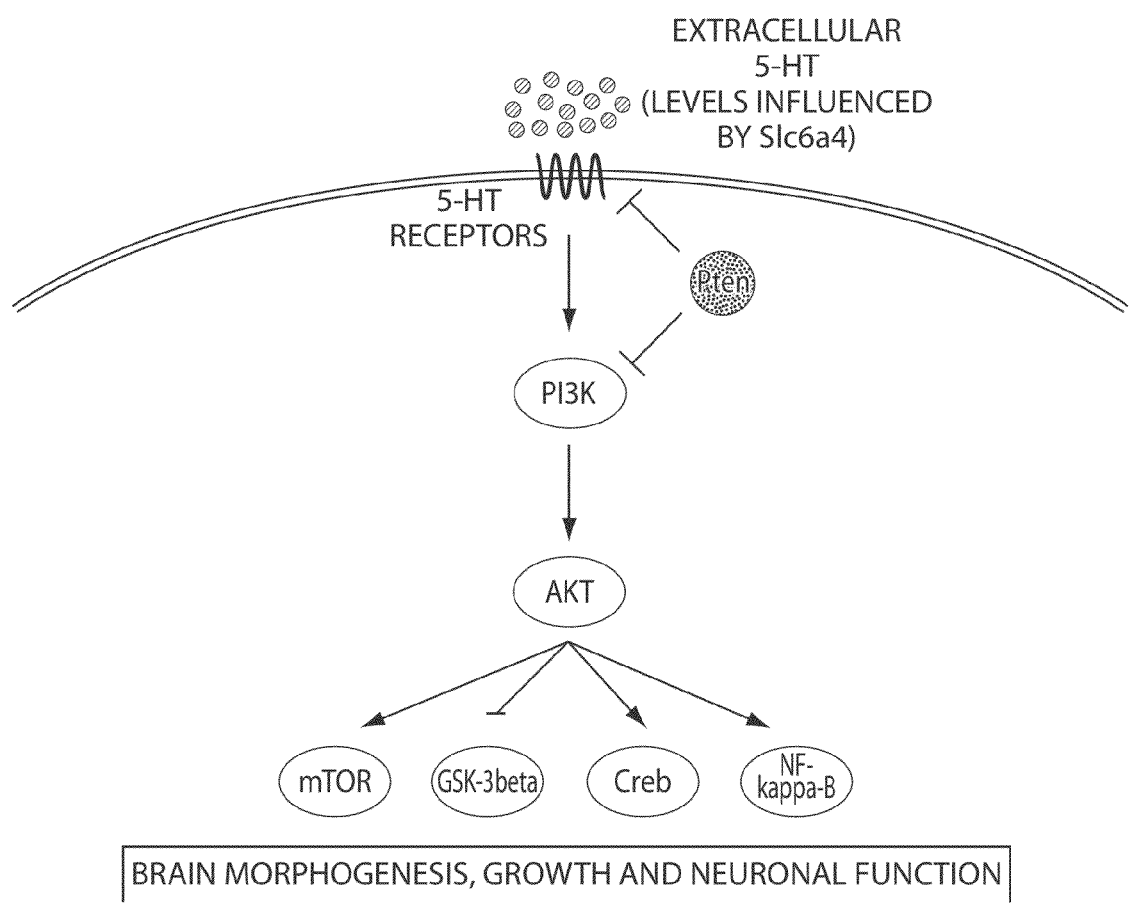

FIG. 7: A model for how the serotonin and PI3K signaling pathways may interact via Slc6a4 and Pten to influence brain size and sociability. Slc6a4 influences the amount of extracellular serotonin (5-HT) available to serotonin receptors. Pten binds 5-HT2C receptor and antagonizes its function. Serotonin signaling can also activate the PI3K pathway. Proposed downstream effectors include mTOR, GSK-3beta, Creb, and NF-KappaB, all of which are capable of influencing brain morphogenesis, growth and neuronal function.

It is to be understood that the drawings are illustrative only and are not required for enablement of the invention.

DETAILED DESCRIPTION OF THE INVENTION

Two genes that give insight into idiopathic autism are PTEN and SLC6A4. PTEN acts as a negative regulator of the PI3-kinase (PI3K) pathway (1). Heterozygous PTEN mutations have been identified in a subset of individuals with autism and macrocephaly, thus rendering affected individuals PTEN haploinsufficient (2-5). The clinical-phenotypic presentation of cognitive impairment in PTEN haploinsufficient individuals is varied. Thus, it has been suggested that individuals with autism spectrum disorder (ASD) who carry PTEN mutations may represent a sensitized group in which to screen for second-site genetic modifiers of the ASD clinical phenotype (4). SLC6A4 encodes membrane-bound transporter of serotonin that influences extracellular levels of this neurotransmitter. SLC6A4 has been implicated as both an ASD candidate susceptibility gene and second-site genetic modifier in ASD (6, 7). Brain overgrowth (8) and severe social behavioral impairments (9) have been reported in individuals with ASD carrying low-expressing Slc6a4 promoter polymorphism alleles. Furthermore, SLC6A4 regulates extracellular serotonin levels, and one of the most replicated reports of a peripheral biomarker in ASD is increased levels of extracellular serotonin in individuals with ASD (6). ELISA assays and similar immunosorbent assays can be used to assay circulating serotonin levels. Levels of serotonin that have been associated with ASD are ≥2 standard deviations above control (non-ASD) population means.

Given their implications for ASD, both PTEN and SLC6A4 are potential peripheral biomarkers in that both genes are pleiotropic, with expression and function outside of the CNS. However, the effects of altered levels of expression of these markers need to be validated against biological and behavioral measures. There is evidence suggesting that the serotonin pathway (in which Slc6a4 acts) intersects with the PI3K pathway (on which Pten acts) in the brain. Evidence has been found for a physical interaction between Pten and the serotonin receptor 5-HT2c, with the phosphatase activity of Pten regulating the activity of this receptor (10). Furthermore, several studies in neural and non-neural cells have demonstrated that Akt is activated by serotonin receptor agonists, and that this activation occurs in a PI3K-dependent manner (reviewed in (11)). However, while the serotonin and PI3K pathways are both strongly implicated in the pathogenesis of ASD, the significance of these interactions for ASD-relevant biological and behavioral phenotypes is not clear at present.

In Cowden syndrome patients, a subset of whom have ASD, missense mutations in PTEN tend to cluster in the core catalytic phosphatase domain of exon 5, and these tend to inactivate the phosphatase function of the protein (12). As a mouse model that approximates these genetic lesions, we have made use of a previously generated Pten mutant line in which exon 5, and thus the core catalytic phosphatase domain, is deleted (13). Mice homozygous for this mutant allele are not viable; however, mice heterozygous for this allele survive into adulthood, thus making these a tenable tool for investigating the developmental outcomes of Pten haploinsufficiency on brain structure and function, as well for screening for second-site genetic and environmental modifiers of such phenotypes. In addition to PTEN, mutations in other repressors of the PI3-kinase pathway have also been associated with ASD, specifically the tuberous sclerosis complex genes TSC1 and TSC2 (14), as well as Neurofibromin 1 (15, 16). Thus, Pten haploinsufficient mice represent a generally useful tool in which a signaling pathway enriched amongst ASD candidate genes, the PI3-kinase pathway, is sensitized. These mice also provide an opportunity to explore broader issues of gene-environment interactions in influencing brain size and behavioral measures relevant to autism.

Based on these observations, we have determined that antagonists or inhibitors of the 5-HT2c receptor signaling pathway unexpectedly restore function in Pten haploinsufficient mice and, accordingly, are useful as autism spectrum disorder therapeutics.

Thus, the invention involves, in some aspects, administering an effective amount of one or more antagonists or inhibitors of the 5 HT2c receptor signaling pathway to a subject having an autism spectrum disorder or believed to have an autism spectrum disorder, to treat the subject. The term "treatment" or "treat" is intended to include prophylaxis, amelioration, prevention or cure of a condition. Treatment after a condition has stated aims to reduce, ameliorate or altogether eliminate the condition, and/or one or more of its associated symptoms, or prevent it from becoming worse. Treatment of subjects before a condition has started (i.e., prophylactic treatment) aims to reduce the risk of developing the condition and/or lessen its severity if the condition later develops. As used herein, the term "prevent" refers to the prophylactic treatment of subjects who are at risk of developing a condition which treatment results in a decrease in the probability that the subject will develop the condition, or results in an increase in the probability that the condition is less severe than it would have been absent the treatment. Treatments may reduce, ameliorate or altogether eliminate the condition, and/or one or more of its associated symptoms, or prevent it from becoming worse, of subjects having the condition as compared to subjects not treated as described herein in accordance with the invention.

A "subject" shall mean a human or animal including, but not limited to, a dog, cat, horse, cow, pig, sheep, goat, chicken, rodent, e.g., rats and mice, and primate, e.g., monkey. Preferred subjects are human subjects. The human subject may be a pediatric, adult or a geriatric subject.

The subject can be known to have a particular autism spectrum disorder, that is amenable to such therapy, or may be believe to have such a disorder. In some embodiments, the subject is free of symptoms otherwise calling for treatment with the antagonists or inhibitors of the 5 HT2c receptor signaling pathway.

Autism spectrum disorders (ASD) are clinically diagnosed disorders with both single and complex multi-gene etiology. Autism spectrum disorders, which are characterized by varying degrees of impairment in communication skills, social interactions, and restricted, repetitive and stereotyped patterns of behavior, include autism, PDD-NOS (pervasive developmental disorder not otherwise specified), Asperger syndrome, Rett syndrome and childhood disintegrative disorder (see Diagnostic and Statistical Manual of Mental Disorders, DSM-IV).

Several screening instruments are known in the art for evaluating a subject's social and communicative development and thus can be used as aids in screening for and diagnosing of autism spectrum disorder. These include the Checklist of Autism in Toddlers (CHAT), the modified Checklist for Autism in Toddlers (M-CHAT), the Screening Tool for Autism in Two-Year-Olds (STAT), the Social Communication Questionnaire (SCQ)(for children 4 years of age and older), the Autism Spectrum Screening Questionnaire (ASSQ), the Australian Scale for Asperger's Syndrome, and the Childhood Asperger Syndrome Test (CAST).

Typically, diagnostic evaluation can include neurologic and genetic assessment, along with in-depth cognitive and language testing. Additional measures developed specifically for diagnosing autism include the Autism Diagnosis Interview-Revised (ADI-R), the Autism Diagnostic Observation Schedule (ADOS-G) and the Childhood Autism Rating Scale (CARS).

The methods described herein have broader application to other disorders in addition to autism spectrum disorders. The methods can be used also for the treatment of bipolar disorder, schizophrenia, obsessive-compulsive disorder, and a range of related personality and mood disorders.

As described herein, autism spectrum disorders are treated with an antagonist or inhibitor of the 5-HT2c (serotonin) receptor pathway, which may be referred to herein equivalently as either an antagonist or an inhibitor individually. An "antagonist or inhibitor of the 5-HT2c receptor signaling pathway", as used herein, is any molecule that partially or fully, blocks, inhibits, or neutralizes a biological activity of the 5-HT2c receptor signaling pathway or the PI3K signaling pathway. Such antagonists or inhibitors may act on an individual polypeptide of the 5-HT2c receptor signaling pathway or the PI3K signaling pathway in a manner that reduces or increases activity of the individual polypeptide, with the effect being an antagonism or inhibition of signaling via the 5-HT2c receptor signaling pathway or the PI3K signaling pathway. For example, an antagonist or inhibitor of the 5-HT2c receptor signaling pathway or the PI3K signaling pathway may be (1) an antagonist or inhibitor of 5-HT2c receptor, phosphoinositol-3 kinase (PI3K), Akt (protein kinase B/PKB), mTOR, Creb or NF-kappa B, or (2) an agonist or activator of GSK-3beta. The antagonist or inhibitor also may be an inverse agonist, e.g., a molecule having a negative efficacy at a polypeptide of the 5-HT2c receptor signaling pathway, such as the 5-HT2c receptor. See FIG. 7 for a schematic depiction of the 5-HT2c receptor signaling pathway.

While 5-HT2c activation (inhibition) is an important activator (inhibitor) of the PI3K signaling pathway, this pathway is known in the art to include more elements than are shown in FIG. 7. An additional activator of the PI3K signaling pathway is IGF1 activation of the IGF1 receptor. Therefore IGF1 and related molecules could be used in the manner described herein for treatment of autism spectrum disorders, more particularly the subset of autism spectrum disorders identified herein. Suitable IGF1 and related therapeutic molecules are described in WO 2008/153929 (the disclosure of which is incorporated herein by reference), for example on pages 12-17.

In additional embodiments, PPAR-gamma agonists (e.g., Thiazolidinediones (TZDs) including rosiglitazone (Avandia), pioglitazone (Actos), troglitazone (Rezulin), MCC-555, rivoglitazone, and ciglitazone) can be used in the methods described herein (as primary thereapeutic, particularly for the subsets of ASD identified herein or as a second therapeutic) to treat individuals with PTEN or SLC6A4 deficiency given that such molecules antagonize the PI3K pathway via transcriptional upregulation of PTEN (see, e.g., Zhang et al., Cancer Biol Ther. 2006. (8):1008-14; Teresi et al., Int J Cancer. 2006. 118(10):2390-8; Patel et al., Curr Biol. 2001. 11(10):764-8).

Suitable antagonists or inhibitors include small molecules (particularly small organic molecules), antagonist antibodies or antigen binding fragments thereof, fragments or amino acid sequence variants of native components of the 5-HT2c receptor signaling pathway, peptides, nucleic acids that induce RNA interference to reduce expression of polypeptides of the 5-HT2c receptor signaling pathway, antisense oligonucleotides, etc. Methods for identifying antagonists or inhibitors include contacting a polypeptide of the 5-HT2c receptor signaling pathway with a candidate molecule and measuring a detectable change in one or more biological activities normally associated with the polypeptide. Other methods for identifying antagonists or inhibitors include contacting a cell with a candidate molecule and measuring a detectable change in expression of a polypeptide of the 5-HT2c receptor signaling pathway, or a nucleic acid that encodes a polypeptide of the 5-HT2c receptor signaling pathway.

Exemplary antagonists or inhibitors of the 5-HT2c receptor include SB 242084 (6-Chloro-5-methyl-1-[[2-(2-methylpyrid-3-yloxy)pyrid-5-yl]carbamoyl]indoline)(see, e.g., Bromidge et al., J. Med. Chem. 40: 3494-3496, 1997; Kennett et al., Neuropharmacology 36: 609-620, 1997); SB 243213 (5-methyl-1-[[-2-[(2-methyl-3-pyridyl)oxy]-5-pyridyl]carbamoyl]-6-trifluoromethylindoline hydrochloride)(see, e.g., Wood et al., Neuropharmacology. 41(2):186-199, 2001); RS 102221 (N-{5-[5-(2,4-dioxo-1,3,8-triazaspiro [4.5]dec-8-yl) pentanoyl]-2,4-dimethoxyphenyl}-4-(trifluoromethyl)benzenesulfonamide)(see, e.g., Bonhaus et al., Neuropharmacology. 36: 621-629, 1997); SB 206553; SB 200646A; SB 221284; SB 204741; SB 228357; SB 200646; VALDOXAN® (agomelatine; S 20098)(see, e.g., Loo et al., Int Clin Psychopharmacol 2002 Sep;17(5):239-47); ketanserine (Bonanno et al., Eur J Pharmacol 126: 317-321); ritanserine; azamianserine; (+)-trans-1-(5-chloro-3-(4-fluorophenyl)-1-indanyl)-4-(2-(3-isopropyl-2-imidazolidinon-1-yl)ethyl)-piperazine; 2,5 -dimethyl-3-(4-fluorophenyl)-1-[1-[2-(imidazolidin-2-on-1-yl)ethyl]-piperidin-4-yl]-1H-indole; fluoxetine; deramciclane; mirtazepine; mianserine; nefazodone; trazodone; YM 35992; Ro 60-0759 ((+)-trans-8-Ethyl-7-hydroxy-9-methoxy-2-methyl-1,3,4,4a,5,10b-hexahydrobenzo[h]isoquinolin-6(2H)-one); Org 38457; Org 12962; EGIS 8465; EGIS-9933; antipsychotics having effect at 5-HT2c receptors, e.g. sertindole, olanzapine and risperidone; LY 53857; metergoline; mesulergine; pireperone; spiroperone; clozapine; dapoxetine; methysergide; serazapine; Ro 60-0491 (N-(2-naphthyl)-N'-(3-pyridyl)urea 1:1 HCl, N-(2-naphthyl)-N'-(3-pyridyl)-urea hydrochloride); S16924; cyamemazine; naphtoxazine (SDZ NVI-085); 532006 (Dekeyne et al., Psychopharmacologia 199: 549-568, 2008) and additional antagonist or inhibitor molecules as described in WO 96/23783, WO 97/48699, WO 97/48700, WO 2002/014273, EP1782813, Hamprecht et al., Bioorg. Med. Chem. Lett. 17(2):424-7 (2007), Hamprecht et al., Bioorg. Med. Chem. Lett. 17(2):428-33 (2007), and Bromidge et al., Bioorg Med Chem Lett. 10(16):1867-1870 (2000).

It is noted that some molecules previously described as useful for treating autism spectrum disorders may function as antagonists or inhibitors of the 5-HT2c receptor signaling pathway or the PI3K signaling pathway. These molecules, such as risperidone, olanzapine, ziprasidone, fluoxetine and PPAR-gamma agonists (e.g., as described herein), are excluded from use in certain of the methods of treating autism spectrum disorders as described herein. These molecules, such as risperidone, olanzapine, ziprasidone, fluoxetine and PPAR-gamma agonists (e.g., as described herein), are excluded from use (other than as second therapeutic molecules) in certain of the methods of treating autism spectrum disorders as described herein. Thus in certain embodiments, such molecules are used as a primary treatment of those ASD individuals who are haploinsufficient for Pten or Slc6a4 and/or as a second therapeutic molecule for treatment of any ASD individual.

In a certain embodiments, a 5-HT2c receptor antagonist or inhibitor is SB 242084 or RS 102221.

In some embodiments, the 5-HT2c receptor antagonist or inhibitor has more than 5-fold selectivity, more than 10-fold selectivity, more than 20-fold selectivity, more than 30-fold selectivity, more than 40-fold selectivity, more than 50-fold selectivity, more than 60-fold selectivity, more than 70-fold selectivity, more than 20-fold selectivity, more than 80-fold selectivity, more than 90-fold selectivity, more than 100-fold selectivity, or more than 150-fold selectivity over 5-HT2a and/or 5-HT2b receptors. In certain embodiments, the 5-HT2C receptor antagonist or inhibitor has like selectivity over other 5-HT, dopamine and adrenergic receptors.

Exemplary antagonists or inhibitors of phosphoinositol-3 kinase (PI3K) include: LY294002 (2-(4-morpholinyl)-8-phenyl-4H-1-benzopyran-4-one); wortmannin; SU6668 (3-[2,4-dimethyl-5-(2-oxo-1,2-dihydro-indol-3-ylidenemethyl)-1H-pyrrol-3-yl]-propionic acid); sunitinib malate (SU11248, SUTENT®); genistein (4',5,7-trihydroxyisoflavone); PX-866 (Ihle et al., Mol Cancer Ther, 4(9), 1349-1357, 2005); XL147 (Exelixis) and additional PI3K antagonists as described in US published applications 2008/0306057 A1 (see, e.g., paragraphs [0079] and [0106]-[0288], the claims, and published application cited therein), and 2008/0293706 A1 (see, e.g., paragraphs [0493]-[0494] and the claims).

Akt is also known as Protein Kinase B (PKB). An Akt antagonist or inhibitor may be an antagonist or inhibitor of Akt1, Akt2 and/or Akt3. Exemplary antagonists or inhibitors of include: LY294005 (1L-6-hydroxymethyl-chiro-inositol 2(R)-2-O-methyl-3-O-octadecylcarbonate); clozapine, ALX-349 (Alexis Biochemical; San Diego, Calif.); VQD-002 (triciribine phosphate monohydrate, VioQuest Pharmaceuticals); phosphatidylinositol ether lipid analogs; Nelfinavir (VIRACEPT); Akt/protein kinase B signaling inhibitor-2 (Yang et al., Cancer Res, 64(13), 4394-4399, 2004); and additional Akt antagonists described in WO 2006/113837, Zhu et al., Bioorg. Med Chem Lett. 16: 3150-3155 (2006), and Lindsley et al., Current Cancer Drug Targets. 8(1): 7-18 (2008).

mTOR antagonists include rapamycin (sirolimus); temsirolimus (CCI-779, Wyeth; Nat Genet. 2004;36:585-95; J Clin Oncol. 2004;22:2336-47); everolimus (RAD001, Novartis); deforolimus (AP23573, ARIAD Pharmaceuticals); zotarolimus (ABT-578); SDZ RAD (40-O(2-hydroxyethyl)-rapamycin); and rapamycin prodrugs and analogs as described in WO 2008/027013.

NV-128 (Novogen Limited) uncouples the Akt-mTOR/p70s6k signal transduction cascade).

Creb antagonists, NF-kappa-B antagonists and GSK-3beta agonists also can be used in the treatment methods described herein.

In all embodiments, antagonists that can pass the into the brain (e.g., cross the blood-brain barrier) are preferred.

Various alternative forms of the antagonists or inhibitors of the 5-HT2c receptor signaling pathway, such as salts, solvates, or polymorphs of the small organic molecules described herein are also useful for treating autism spectrum disorders as described herein. Such alternative forms will be known to the person of skill in the art.

In certain embodiments antagonists or inhibitors of the 5-HT2c receptor signaling pathway are molecules that induce RNA interference, such as short interfering nucleic acids (siNA) specific for a gene transcript of a polypeptide in the 5-HT2c receptor signaling pathway. For example, gene products of genes that are described herein as suitably antagonized or inhibited in the therapeutic methods (e.g., 5-HT2c receptor, PI3K, Akt, mTOR, Creb and NF-kappa B) can be inhibited in this manner. The siNA(s) reduce the amount of mRNA and protein of the polypeptide in the 5-HT2c receptor signaling pathway, and thereby inhibit the 5-HT2c receptor signaling pathway.

Inhibitor molecules that are short interfering nucleic acids (siNA), which include, short interfering RNA (siRNA), double-stranded RNA (dsRNA), micro-RNA (miRNA), and short hairpin RNA (shRNA) molecules are used to inhibit the expression of target genes. The siNAs of the present invention, for example siRNAs, typically regulate gene expression via target RNA transcript cleavage/degradation or translational repression of the target messenger RNA (mRNA). In one embodiment siRNAs are exogenously delivered to a cell. In a specific embodiment siRNA molecules are generated that specifically target 5-HT2c receptor, phosphoinositol-3 kinase (PI3K), Akt (protein kinase B/PKB), mTOR, Creb or NF-kappa B.

A short interfering nucleic acid (siNA) of the invention can be unmodified or chemically-modified. A siNA of the instant invention can be chemically synthesized, expressed from a vector or enzymatically synthesized. The instant invention also features various chemically-modified synthetic short interfering nucleic acid (siNA) molecules capable of inhibiting gene expression or activity in cells by RNA interference (RNAi). The use of chemically-modified siNA improves various properties of native siNA molecules through, for example, increased resistance to nuclease degradation in vivo and/or through improved cellular uptake. Furthermore, siNA having multiple chemical modifications may retain its RNAi activity. For example, in some cases, siRNAs are modified to alter potency, target affinity, the safety profile and/or the stability to render them resistant or partially resistant to intracellular degradation. Modifications, such as phosphorothioates, for example, can be made to siRNAs to increase resistance to nuclease degradation, binding affinity and/or uptake. In addition, hydrophobization and bioconjugation enhances siRNA delivery and targeting (De Paula et al., RNA. 13(4): 431-56, 2007) and siRNAs with ribo-difluorotoluyl nucleotides maintain gene silencing activity (Xia et al., ASC Chem. Biol. 1(3):176-83, (2006). siRNAs with amide-linked oligoribonucleosides have been generated that are more resistant to S1 nuclease degradation (Iwase R et al. 2006 Nucleic Acids Symp Ser 50: 175-176). In addition, modification of siRNA at the 2'-sugar position and phosphodiester linkage confers improved serum stability without loss of efficacy (Choung et al., Biochem. Biophys. Res. Commun. 342(3):919-26, 2006). In one study, 2'-deoxy-2'-fluoro-beta-D-arabinonucleic acid (FANA)-containing antisense oligonucleotides compared favorably to phosphorothioate oligonucleotides, 2'-O-methyl-RNA/DNA chimeric oligonucleotides and siRNAs in terms of suppression potency and resistance to degradation (Ferrari N et a. 2006 Ann N Y Acad Sci 1082: 91-102).

In some embodiments an siNA is an shRNA molecule encoded by and expressed from a genomically integrated transgene or a plasmid-based expression vector. Thus, in some embodiments a molecule capable of inhibiting gene expression is a transgene or plasmid-based expression vector that encodes a small-interfering nucleic acid. Such transgenes and expression vectors can employ either polymerase II or polymerase III promoters to drive expression of these shRNAs and result in functional siRNAs in cells. The former polymerase permits the use of classic protein expression strategies, including inducible and tissue-specific expression systems. In some embodiments, transgenes and expression vectors are controlled by tissue specific promoters. In other embodiments transgenes and expression vectors are controlled by inducible promoters, such as tetracycline inducible expression systems. Examples of making and using such hairpin RNAs for gene silencing in mammalian cells are described in, for example, (Paddison et al., Genes Dev, 2002, 16:948-58; McCaffrey et al., Nature, 2002, 418:38-9; McManus et al., RNA 2002, 8:842-50; Yu et al., Proc Natl Acad Sci USA, 2002, 99:6047-52).

One embodiment herein contemplates the use of gene therapy to deliver one or more expression vectors, for example viral-based gene therapy, encoding one or more small interfering nucleic acids, capable of inhibiting expression of, for example, 5-HT2c receptor, phosphoinositol-3 kinase (PI3K), Akt (protein kinase B/PKB), mTOR, Creb or NF-kappa B. As used herein, gene therapy is a therapy focused on treating genetic diseases, such as cancer, by the delivery of one or more expression vectors encoding therapeutic gene products, including shRNAs, to diseased cells. Methods for construction and delivery of expression vectors will be known to one of ordinary skill in the art.

The present invention, thus, contemplates in vitro use of siRNAs (shRNAs, etc.) as well as in vivo pharmaceutical preparations containing siRNAs (shRNAs, etc.) that may be modified siRNAs (shRNAs, etc.) to increase their stability and/or cellular uptake under physiological conditions, that specifically target nucleic acids encoding, for example 5-HT2c receptor, phosphoinositol-3 kinase (PI3K), Akt (protein kinase B/PKB), mTOR, Creb or NF-kappa B, together with pharmaceutically acceptable carriers.

In certain embodiments antagonists or inhibitors of the 5-HT2c receptor signaling pathway are antisense nucleic acids. Antisense nucleic acids include short oligonucleotides as well as longer nucleic acids. Preferably the antisense nucleic acids are complementary to and bind to portions of the coding sequence or 5' nontranslated sequence of one or more polypeptides in the 5-HT2c receptor signaling pathway, thereby inhibiting translation of functional polypeptide. Other antisense nucleic acids which reduce or block transcription are also useful.

Thus the invention embraces antisense oligonucleotides that selectively bind to a nucleic acid molecule encoding polypeptide(s) in the 5-HT2c receptor signaling pathway, to reduce the expression (transcription or translation) of the polypeptide(s). As used herein, the term "antisense oligonucleotide" describes an oligonucleotide that is an oligoribonucleotide, oligodeoxyribonucleotide, modified oligoribonucleotide, or modified oligodeoxyribonucleotide which hybridizes under physiological conditions to DNA comprising a gene encoding 5-HT2c receptor, phosphoinositol-3 kinase (PI3K), Akt (protein kinase B/PKB), mTOR, Creb or NF-kappa B, and, thereby, inhibits the transcription of that gene and/or the translation of that mRNA.

Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon the sequences of 5-HT2c receptor, phosphoinositol-3 kinase (PI3K), Akt (protein kinase B/PKB), mTOR, Creb or NF-kappa B nucleic acids, including allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840-844, 1996). Most preferably, the antisense oligonucleotides comprise a complementary sequence of 20-30 bases.

Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439-457, 1994) and at which proteins are not expected to bind. Finally, one of ordinary skill in the art may easily derive cDNA sequences and genomic DNA corresponding to polypeptide(s) in the 5-HT2c receptor signaling pathway from databases and published literature. Thus, the present invention also provides for antisense oligonucleotides which are complementary to the genomic DNA corresponding to nucleic acids encoding 5-HT2c receptor, phosphoinositol-3 kinase (PI3K), Akt (protein kinase B/PKB), mTOR, Creb or NF-kappa B. Similarly, antisense to allelic or homologous cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates in vitro use of antisense molecules as well as in vivo pharmaceutical preparations containing modified antisense molecules that are complementary to and hybridizable with, under physiological conditions, nucleic acids encoding 5-HT2c receptor, phosphoinositol-3 kinase (PI3K), Akt (protein kinase B/PKB), mTOR, Creb or NF-kappa B, together with pharmaceutically acceptable carriers.

In another embodiment, the antisense nucleic acids of the invention may be produced by expression in cells by expression vectors introduced therein. The choice and design of an appropriate vector is within the ability and discretion of one of ordinary skill in the art.

Expression vectors containing all the necessary elements for expression are commercially available and known to those skilled in the art. See, e.g., Sambrook et al., Molecular Cloning: A Laboratory Manual, Second Edition, Cold Spring Harbor Laboratory Press, 1989. According to this embodiment, cells are genetically engineered by the introduction into the cells of heterologous DNA (RNA) encoding antisense nucleic acid. The antisense nucleic acid is placed under operable control of transcriptional elements to permit the expression of the antisense nucleic acid in the host cell. Additional vectors for delivery of antisense nucleic acids will be known to one of ordinary skill in the art.

Various techniques may be employed for introducing antisense nucleic acids into cells in accordance with the invention, depending on whether the nucleic acids are introduced in vitro or in vivo in a host. Such techniques include transfection of nucleic acid-CaPO$_4$ precipitates, transfection of nucleic acids associated with DEAE, transfection or infection with viruses including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, adenovirus or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. Where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

In certain embodiments antagonists or inhibitors of the 5-HT2c receptor signaling pathway are antibodies, or antigen-binding fragments thereof that specifically bind to a polypeptide of this pathway, which leads to a reduction in the catalytic activity of the polypeptide.

The antibodies of the present invention are prepared by any of a variety of methods, including administering a protein, fragments of a protein, cells expressing the protein or fragments thereof and the like to an animal to induce polyclonal antibodies. The production of monoclonal antibodies is performed according to techniques well known in the art. It is well-known in the art that only a small portion of an antibody molecule, the paratope, is involved in the binding of the antibody to its epitope (see, in general, Clark, W. R., 1986, *The Experimental Foundations of Modern Immunology*, Wiley & Sons, Inc., New York; Roitt, I., 1991, *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab')2 fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762, and 5,859,205. Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans. Thus, as will be apparent to one of ordinary skill in the art, the present invention also provides for F(ab')2, Fab, Fv, and Fd fragments; chimeric antibodies in which the Fc and/or FR and/or CDR1 and/or CDR2 and/or light chain CDR3 regions have been replaced by homologous human or non-human sequences; chimeric F(ab')2 fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies, domain antibodies and heavy chain antibodies.

Thus, the invention involves polypeptides of numerous size and type that bind specifically to polypeptides of the 5-HT2c receptor signaling pathway and inhibit functional activity. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptides and non-peptide synthetic moieties.

Antagonists or inhibitors of the 5-HT2c receptor signaling pathway are administered in an amount effective to treat the autism spectrum disorder in the subject. An effective amount is a dosage of the therapeutic molecule(s) sufficient to provide a medically desirable response. For example the desirable response may be inhibiting the progression of the autism spectrum disorder. This may involve only slowing the progression of the autism spectrum disorder temporarily, although more preferably, it involves halting the progression of the autism spectrum disorder permanently. This can be monitored by routine diagnostic methods known to those of ordinary skill in the art.

It should be understood that the therapeutic molecules of the invention are used to treat or prevent the autism spectrum disorder, that is, they may be used prophylactically in subjects at risk of developing the autism spectrum disorder. Thus, an effective amount is that amount which can lower the risk of, lessen the severity of, or perhaps prevent altogether the development of the autism spectrum disorder.

The factors involved in determining an effective amount are well known to those of ordinary skill in the art and can be addressed with no more than routine experimentation. It is generally preferred that a maximum dose of the therapeutic molecules of the invention (alone or in combination with other therapeutic molecules or treatment regimens) be used, that is, the highest safe dose according to sound medical judgment. It will be understood by those of ordinary skill in the art however, that a patient may insist upon a lower dose or tolerable dose for medical reasons, psychological reasons or for virtually any other reasons.

Antagonists or inhibitors of the 5-HT2c receptor signaling pathway may be administered alone, in a pharmaceutical composition or combined with other therapeutic molecule(s) or treatment regimens. Optionally other therapeutic molecule(s) may be administered simultaneously or sequentially. When the other therapeutic molecule(s) are administered simultaneously they can be administered in the same or separate formulations, but are administered at the same time. The other therapeutic molecule(s) may be administered sequentially with one another and with the antagonists or inhibitors of the 5-HT2c receptor signaling pathway when the administration of the other therapeutic molecule(s) and the antagonists or inhibitors of the 5-HT2c receptor signaling pathway are temporally separated. The separation in time between the administration of these molecules may be a matter of minutes or it may be longer, such as 1, 2, 3, 4, 5, 6, 7, 8, 9, 10, 11 or 12 hours, or more, including 1, 2, 3, 4, 5, 6, 7 days or more.

The pharmaceutical compositions used in the methods of the invention are preferably sterile and contain effective amounts of the antagonists or inhibitors of the 5-HT2c receptor signaling pathway for producing the desired response in a unit of weight or volume suitable for administration to a subject. The doses of antagonists or inhibitors of the 5-HT2c receptor signaling pathway administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The dosage of one or more antagonists or inhibitors of the 5-HT2c receptor signaling pathway may be adjusted by the individual physician or veterinarian, particularly in the event of any complication. A therapeutically effective amount typically varies from 0.01 mg/kg to about 1000 mg/kg, preferably between about 0.1-10 mg/kg, such as between about 0.1-1 mg/kg/day or between about 1-10 mg/kg/day, in one or more dose administrations daily, for one or more days.

Various modes of administration are known to those of ordinary skill in the art which effectively deliver the pharmacological agents to a desired tissue, cell, or bodily fluid. Administration of the molecules of the invention includes, but is not limited to, oral, intravenous, subcutaneous, intramuscular, topical, depot injection, implantation, time-release mode, intracavity, intranasal, inhalation, intrathecal, intraocular, and controlled release. In some embodiments, the pharmaceutical compositions of the invention are introduced parenterally, transmucosally (e.g., orally), nasally, intrathecally, rectally, intravaginally, sublingually, submucosally, or transdermally. Parenteral administration is administration not through the alimentary canal but rather through some other route via, for example, intravenous, subcutaneous, intramuscular, intrathecal, intraperitoneal, intraorbital, intracapsular, intraspinal, intrasternal, intra-arterial, or intradermal administration. For the small organic molecules described herein, oral administration is preferred. The skilled artisan can appreciate the specific advantages and disadvantages to be considered in choosing a mode of administration.

The invention is not limited by the particular modes of administration disclosed herein. Standard references in the art (e.g., *Remington's Pharmaceutical Sciences*, 20th Edition, Lippincott, Williams and Wilkins, Baltimore Md., 2001) provide modes of administration and formulations for delivery of various pharmaceutical preparations and formulations in pharmaceutical carriers. Other protocols which are useful for the administration of pharmacological agents of the invention will be known to one of ordinary skill in the art, in which the dose amount, schedule of administration, sites of administration, mode of administration and the like vary from those presented herein.

Administration of pharmacological agents of the invention to mammals other than humans, e.g., for testing purposes or veterinary therapeutic purposes, is carried out under substantially the same conditions as described above. It will be understood by one of ordinary skill in the art that this invention is applicable to both human and animal diseases.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic molecules. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

A pharmacological agent or composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the pharmacological agents of the invention, and with each other, in a manner such that there is no interaction which would substantially impair the desired pharmaceutical efficacy.

The pharmaceutical compositions may contain suitable buffering agents, as described above, including: acetate, phosphate, citrate, glycine, borate, carbonate, bicarbonate, hydroxide (and other bases) and pharmaceutically acceptable salts of the foregoing compounds. The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well known in the art of pharmacy. All methods include the step of bringing the active agent into association with a carrier, which constitutes one or more accessory ingredients. In general, the compositions are prepared by uniformly and intimately bringing the active compound into association with a liquid carrier, a finely divided solid carrier, or both, and then, if necessary, shaping the product.

The antagonists or inhibitors of the 5-HT2c receptor signaling pathway, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the compounds may be in powder form for constitution with a suitable vehicle (e.g., saline, buffer, or sterile pyrogen-free water) before use.

Compositions suitable for oral administration may be presented as discrete units, such as capsules, tablets, pills, lozenges, each containing a predetermined amount of the active compound(s). Other compositions include suspensions in aqueous liquids or non-aqueous liquids such as a syrup, elixir, an emulsion, or a gel.

Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, sorbitol or cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e., EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the molecule(s) or by release of the biologically active molecule(s) beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e., powder; for liquid forms, a soft gelatin shell may be used. The shell material of cachets could be thick starch or other edible paper. For pills, lozenges, molded tablets or tablet triturates, moist massing techniques can be used.

One may dilute or increase the volume of the therapeutic molecule with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic molecule together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For administration intranasally or by inhalation, the antagonists or inhibitors of the 5-HT2c receptor signaling pathway may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

Also contemplated herein is pulmonary delivery of the antagonists or inhibitors of the 5-HT2c receptor signaling pathway. The molecule(s) are delivered to the lungs of a mammal while inhaling and traverse across the lung epithelial lining to the blood stream.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Nasal (or intranasal) delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The antagonists or inhibitors of the 5-HT2c receptor signaling pathway are suitable for use in a variety of drug delivery systems. For a brief review of methods for drug delivery, see Langer, *Science* 249:1527-1533, 1990, which is incorporated herein by reference.

The antagonists or inhibitors of the 5-HT2c receptor signaling pathway may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug therefrom. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

The invention also contemplates the use of kits. In some aspects of the invention, the kit can include a pharmaceutical preparation vial, a pharmaceutical preparation diluent vial, and the antagonists or inhibitors of the 5-HT2c receptor signaling pathway as described herein. The vial containing the diluent for the pharmaceutical preparation is optional. The diluent vial contains a diluent such as physiological saline for diluting what could be a concentrated solution or lyophilized powder of the molecule(s). The instructions can include instructions for mixing a particular amount of the diluent with a particular amount of the concentrated pharmaceutical preparation, whereby a final formulation for injection or infusion is prepared. The instructions may include instructions for treating a subject with an effective amount of the molecule(s). It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

Also contemplated are diagnostic methods, based on the identification herein of biomarkers for autism spectrum disorders, and the use of such diagnostic methods in combination with therapy. The diagnostic methods may be used to aid in the selection of appropriate therapy and/or patient populations (such as for clinical trials).

The diagnostic methods include evaluating the subject for the presence of biomarkers for autism spectrum disorders, particularly for autism spectrum disorders characterized by increased head size (circumference) and/or deficits in social behavior. The deficit in social behavior is, in some embodiments, a deficit in social interaction and/or a deficit in social memory, as demonstrated herein.

For example, autism spectrum disorder characterized by increased head size (circumference) and deficits in social behavior is demonstrated herein to be is associated with and/or caused by mutations or variations in the Pten gene and/or the Slc6a4 gene resulting in haploinsufficiency of these gene(s) as shown herein. Accordingly, a subject can be screened for such mutations, variations or haploinsufficiency. The diagnostic methods also can include testing the subject for macrocephaly (brain overgrowth) and/or decreased sociability (deficits in social approach behavior).

More specifically, the diagnostic methods include analyzing biological samples for the presence of genetic or epigenetic variations that result in decreased expression or function of PTEN (PTEN deficiency) and/or genetic or epigenetic variations that result in decreased expression or function of SLC6A4 (SLC6A4 deficiency).

The diagnostic methods additionally or alternatively include analyzing biological samples of a subject for increased circulating serotonin. ELISA assays and similar immunosorbent assays can be used to assay circulating serotonin levels. Levels of serotonin that have been associated with ASD are $\geq 2$ standard deviations above control (non-ASD) population means. Additionally, HPLC, mass spectrometry and proteomic arrays can also be used to assay circulating serotonin levels.

The diagnostic methods also may be combined with the therapeutic methods described herein. The combination of diagnostic and therapeutic methods can be used to guide treatment, such as when diagnostic methods are employed in advance of treatment to determine which subjects are treated. The combination of diagnostic and therapeutic methods can be used to follow the course of the treatment and/or the course of the disorder, such as when diagnostic methods are employed during or after treatment to determine the effectiveness of the treatment of the subjects. Such applications of diagnostic methods in combination with therapeutic methods is routinely practiced in the medical arts.

The diagnostic methods can be performed prior to treatment to determine the suitability of the subject for treatment with antagonists or inhibitors of the 5-HT2c receptor signaling pathway as described herein. Subjects having other diseases, conditions and disorders that have this genetic basis and are amenable to the therapies described herein also can be diagnosed and treated in the same way. In particular, subjects with mutations or variations in genes that are targets of the Pten gene and/or the Slc6a4 gene or are downstream of 5-HT2c receptor are amenable to the therapies described herein and can be diagnosed and treated in the same way.

Standard clinical diagnostic methods are well known in the art. Typically these methods include obtaining a sample from the subject, which may be without limitation a tissue sample, biopsy, fluid sample (e.g., blood, urine, saliva, cerebrospinal fluid), etc., and then subjecting the sample to the diagnostic procedure. Many well-known methodologies are available to the practitioner to analyze the sample, such as various nucleic acid detection and amplification methods, including polymerase chain reaction-based methods, and various protein detection methods, including antibody-based detection methods. In other instances it may be possible to use imaging techniques for non-invasive diagnosis.

The present invention is further illustrated by the following Examples, which in no way should be construed as further limiting.

EXAMPLES

Example 1

Haploinsufficiency for Pten and Serotonin Transporter Cooperatively Influences Brain Size and Social Behavior Materials and Methods Animals: Strains used were B6.129-Pten$^{tm1Rps}$ (13) (from the National Cancer Institute at Frederick) and B6.129-Slc6a4$^{tm1Kpl}$ (23) (from Taconic). At their respective facilities, each line was crossed to C57BL/6 background for 10 generations to reach congenicity. We generated mice for this study from two crosses: Pten$^{+/-}$; Slc6a4$^{+/+}$×Pten$^{+/+}$; Slc6a4$^{+/+}$ mice to yield Pten$^{+/+}$; Slc6a4$^{+/+}$ ("wild type") and Pten$^{+/-}$; Slc6a4$^{+/+}$ ("Pten haploinsufficient") mice, and Pten$^{+/-}$; Slc6a4$^{+/+}$×Pten$^{+/+}$; Slc6a4$^{-/-}$ mice to yield Pten$^{+/+}$; Slc6a4$^{+/-}$ ("Slc6a4 haploinsufficient") and Pten$^{+/-}$; Slc6a4$^{+/-}$ ("Pten and Slc6a4 haploinsufficient") mice. We found this approach advantageous over a Pten$^{+/-}$×Slc6a4$^{+/-}$ mating strategy due to elevated rates of embryonic and early postnatal lethality in Pten$^{+/-}$; Slc6a4$^{+/-}$ mice.

Behavioral testing occurred at 8 weeks or 12 weeks of age. All animals were housed in groups of 2-5 mice per cage, with no differences in housing between genotypes. Food and water were freely available and animals were kept on a 12-hour light/dark cycle. All behavioral testing was carried out near the end of the light cycle. Experiments were performed according to a protocol approved by the Massachusetts Institute of Technology Committee on Animal Care and in accordance with NIH guidelines.

Social approach: A mouse was placed in an open top acrylic box (24"L×12"W×12"H) with opaque walls. The box was divided into three (8"L×12"W) chambers separated by opaque acrylic panels with holes providing passage between chambers. For reference, the chambers were numbered, from left to right 1, 2, and 3. In chamber 1, an wild type unfamiliar sex and strain matched mouse was held in a clear cylindrical acrylic cage (4" diameter×8"H) fitted with numerous holes that allow for proper ventilation, as well as visual, tactile, and olfactory contact between the two mice. An identical cage was placed in chamber 3 but left empty. The orientation of the apparatus in the testing room was kept consistent from trial to trail. We have previously found that randomizing the orientation of the apparatus relative to the testing room does not alter results. Prior to testing, the stimulus mouse and the subject mouse were acclimated to the social approach apparatus individually for 5 minutes a day for three days. On the day of testing, the mice were again acclimated to the apparatus for 5 minutes. During this time, the subject mouse was observed for bias toward chambers 1 or 3—no such bias was observed for any genotype. The stimulus mouse was then added to the apparatus and a video recording was taken of a 10-minute trial. The resulting video was scored with computer assistance by importing into ImageJ software (http://rsb.info.nih.gov/ij/), where each chamber was defined as a region of interest using a script written in-house, and the number of frames in which the mouse was in each region of interest was quantified. All data sets were hand-checked by a trained observer blind to genotype to ensure accuracy.

Olfaction: Protocol was adapted from (30, 59). Each mouse was placed into a clean plastic cage identical to the home cage, and allowed 5 minutes to acclimate. A cotton swab moistened with 10 µl of distilled water was inserted through the lid of the cage at a height of 10 cm for one minute. The swab was replaced with a fresh swab twice, for a total of three presentations, then followed with three one minute presentations of swabs moistened with 10 µl vanilla extract (Frontier, Norway, Iowa). After presentation of the vanilla, swabs moistened with 5 µl of lemon extract (Simply Organic, Boulder, Colo.), were presented three times for one minute each. For each swab presentation, the frequency and duration (in seconds) of sniffs less than 3 cm from the swab was recorded.

Prepulse inhibition: We used a ASR-PRO1 acoustic startle reflex test apparatus (Med Associates, St. Albans, Vt.). Prior to testing, mice were acclimated to the testing room for 1 hour. Mice were acclimated to the apparatus for 2 minutes prior to start of trials. Trials were given at an interval of 3-8 seconds (randomized). Trials consisted of either a 40 ms startle stimulus alone (110 db white noise) or a startle stimulus preceded 100 ms earlier by a 20 ms white noise prepulse that was either 8 db, 12 db or 16 db above background (60 bd white noise). 5 trials for each stimulus configuration were recorded using Startle Reflex Software (Med Associates, St. Albans, Vt.).

Results

Figure 1A:
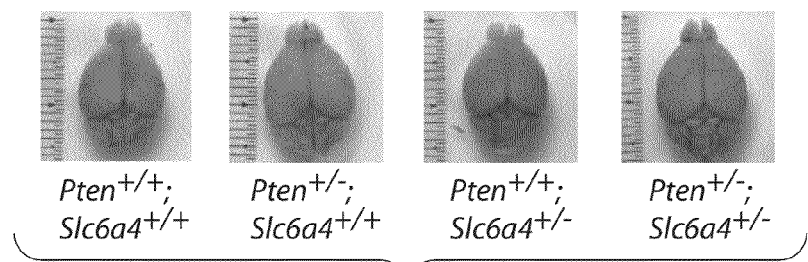
FIG. 1(A) Representative dorsal-view images of brains from male Pten$^{+/+}$; Slc6a4$^{+/+}$, Pten$^{+/-}$; Slc6a4$^{+/+}$, Pten$^{+/+}$; Slc6a4$^{+/-}$ and Pten$^{+/-}$; Slc6a4$^{+/-}$ mice. Brains were collected at 12 weeks of age.
Figure 1B:
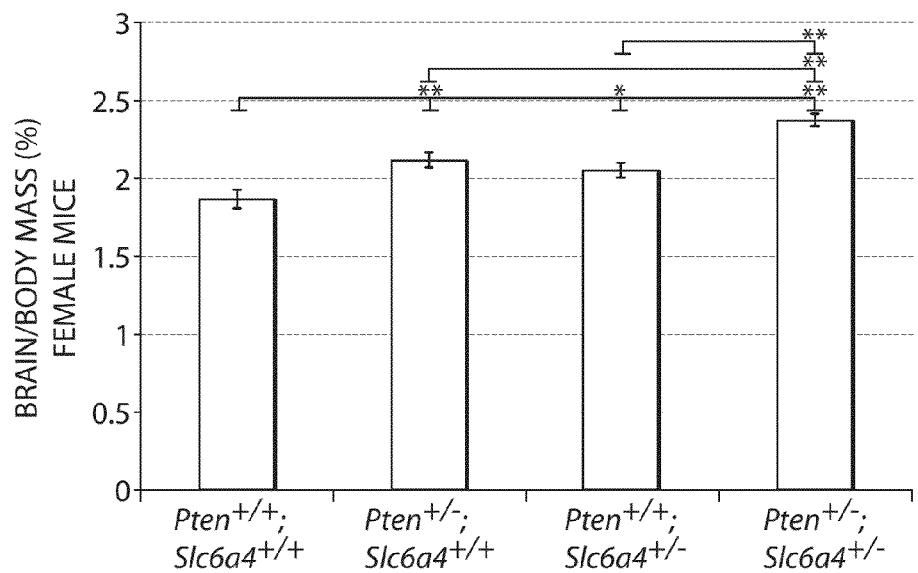
FIGS. 1(B) and (C) As compared to wild type controls, Pten and Slc6a4 haploinsufficient mice show a significant increase in brain mass. (B) Brain mass in females is significantly increased in Pten$^{+/-}$; Slc6a4$^{+/-}$ mice as compared to Pten$^{+/+}$; Slc6a4$^{+/+}$, Pten$^{+/-}$; Slc6a4$^{+/+}$ and Pten$^{+/+}$; Slc6a4$^{+/-}$ mice ($F_{3,42}$=20.6; P<0.001). n=10 Pten$^{+/+}$; Slc6a4$^{+/+}$, 10 Pten$^{+/-}$; Slc6a4$^{+/+}$, 10 Pten$^{+/+}$; Slc6a4$^{+/-}$ and 13 Pten$^{+/-}$; Slc6a4$^{+/-}$ mice. (C) Brain mass in males is significantly increased in Pten$^{+/-}$; Slc6a4$^{+/-}$ mice as compared to Pten$^{+/+}$; Slc6a4$^{+/+}$, Pten$^{+/-}$; Slc6a4$^{+/+}$ and Pten$^{+/+}$; Slc6a4$^{+/-}$ mice ($F_{3,33}$=30.0; P<0.001). n=6 Pten$^{+/+}$; Slc6a4$^{+/+}$, 6 Pten$^{+/-}$; Slc6a4$^{+/+}$, 11 Pten$^{+/+}$; Slc6a4$^{+/-}$ and 11 Pten$^{+/-}$; Slc6a4$^{+/-}$ mice. * P<0.05, ** P<0.01 (Tukey HSD test). Ages were 8-12 weeks. Data are normalized to body mass to account for differences in body mass between animals.
Figure 1C:
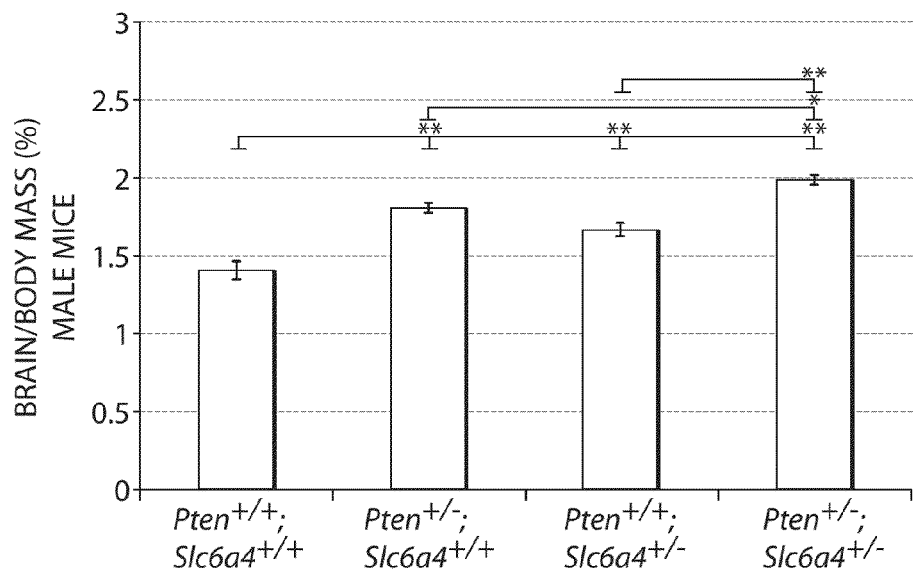
FIG. 1: Macrocephaly in Pten$^{+/-}$; Slc6a4$^{+/-}$ mice.

To test for a potential interaction between Pten and Slc6a4, we first needed to identify a phenotypic readout relevant to ASD. One of the most widely reported neuroanatomical abnormalities reported in ASD is macrocephaly, with an incidence of 10-30% in adulthood and up to 60% during development (17). Studies in ASD patients have shown that brain size is positively correlated with the severity of behavioral phenotypes in ASD-relevant measures (18, 19). Reports from conditional knockouts of Pten in the mouse brain describe macrocephaly phenotypes, with increases in cell soma size and neurite hypertrophy likely contributing to these phenotypes (20-22). We generated Pten and Slc6a4 compound heterozygous mutant mice by crossing Pten haploinsufficient mice to a line carrying a previously described Slc6a4 loss of function allele (23). We focused on germline heterozygous mice to maximize clinical relevance. To examine whether Pten or Slc6a4 haploinsufficient mice exhibit brain overgrowth, we obtained measures of overall brain mass, normalized to body mass to account for variations in body size. These data showed that haploinsufficiency for Pten or Slc6a4 results in a macrocephaly phenotype in both males and females (FIG. 1A-C). Furthermore, Pten$^{+/-}$; Slc6a4$^{+/-}$ mice had an additive brain overgrowth phenotype that is more severe than that seen in either Pten or Slc6a4 haploinsufficient mice (FIG. 1A-C). Although the cellular mechanism underlying effect on growth remains to be identified, these data indicate that Pten and Slc6a4 act cooperatively to influence a phenotype relevant to ASD, brain overgrowth.

Figure 2A:
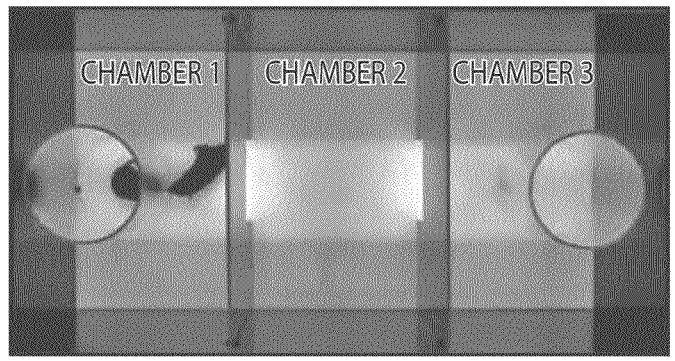
FIG. 2(A) Still images of the apparatus used to assay social approach behavior. A social stimulus mouse resides in an acrylic cage in chamber 1 and the acrylic cage in chamber 3 remains empty as a control. The subject mouse begins the assay in chamber 2, the assay is video-recorded for 10 minutes, and the percent time spent in each chamber is then quantified.
Figure 2B:
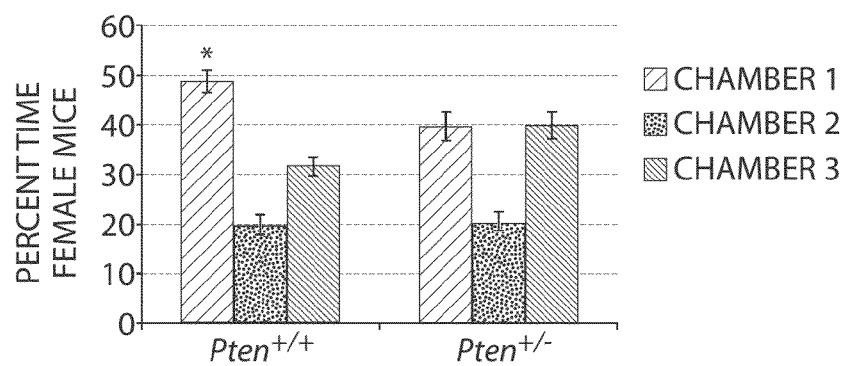
FIGS. 2(B) and (C) Data showing percent time spent in chamber containing a cage that holds a stimulus mouse (chamber 1), empty chamber (chamber 2) or chamber containing a cage with no stimulus mouse (chamber 3). All mice tested were 12 weeks of age. (B) In females, Pten$^{+/+}$ mice show a significant preference for chamber 1 over chamber 3, whereas this preference is not seen in Pten$^{+/-}$ mice. (C) In males, both Pten$^{+/+}$ and Pten$^{+/-}$ mice show a preference for chamber 1 over chamber 3. * P<0.05, ANOVA within group comparison between chamber 1 and chamber 3. n=17 males, 12 females for each genotype. Error bars indicate SEM. In each group of bars, the order is: left bar=chamber 1, middle bar=chamber 2, right bar=chamber 3.
Figure 2C:
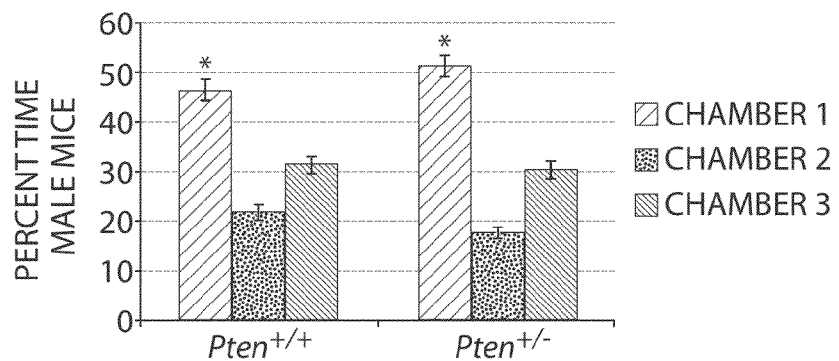
FIG. 2: Behavioral characterization of Pten$^{+/-}$ mice.
FIG. 2(D) Prepulse inhibition of the acoustic startle response in Pten$^{+/-}$ mice. All mice tested were 12 weeks of age. As compared to Pten$^{+/+}$ mice, Pten$^{+/-}$ mice have significant deficits in startle inhibition at prepulses 12 db or 16 db above background. * P<0.05, ANOVA comparison between genotypes for given prepulse intensity. n=12 mice (6 females) for each genotype. In each group of bars, the order is: left bar=Pten$^{+/+}$, right bar=Pten$^{+/-}$.
Figure 2D:
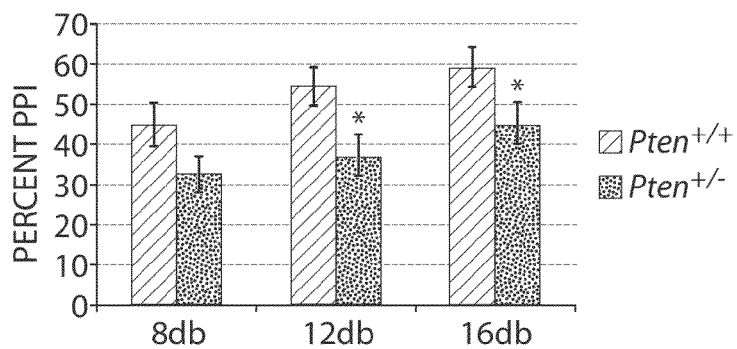

The above results argue that Pten haploinsufficient mice may be a useful tool to examine second site genetic modifiers that interact with Pten in a manner relevant to polygenic ASD, as well as for testing the effects of environmental modifications and the effects of therapeutic compounds. To investigate whether Pten haploinsufficient mice have surface validity for behavioral phenotypes relevant to ASD, we tested 12-week-old mice using several behavior assays. The assays we used tested sociability, which reflects a core diagnostic deficit seen in individuals with ASD (24), as well as prepulse inhibition, a measure of sensorimotor gating which has been reported to be abnormal in individuals with ASD (25-27). To test for a possible confounding factor of olfactory function in social behavior, we exposed Pten haploinsufficient mice and controls to an olfactory habituation-dishabituation test and found that these mice responded normally (FIG. 6), indicating that they do not have a gross impairment in olfactory function. To measure social approach behavior, we used a variation of an apparatus in which mice have to choose between spending time interacting with an unfamiliar gender- and age-matched stimulus mouse or an inanimate object (28, 29) (FIG. 2A). Whereas wild-type mice of both genders showed a significant preference for spending time in the social chamber, Pten haploinsufficient female mice did not show this preference and spent roughly equal time in the social and non-social chambers (FIG. 2B). Male Pten haploinsufficient mice did not show this same deficit in social approach behavior (FIG. 2C). In tests of sensorimotor gating in Pten haploinsufficient mice and controls, we found that both genders had deficits in prepulse inhibition of the acoustic startle response (FIG. 2D). Our results with Pten haploinsufficient mice generally agree with behavioral results from CNS-specific conditional Pten knockout mice (21), in which animals were tested for a variety of ASD-relevant phenotypes. Differences are seen in the initial tendency for social approach in males, where conditional knockouts show a deficit and Pten haploinsufficient mice do not. These differences are most likely attributable to the different nature of the genetic manipulation in these two complementary models. Identifying the neurobiological basis for different behavioral phenotypes in these models should provide insight into how Pten influences the development of neural circuitry relevant to ASD.

To test whether the social approach phenotype we observe in Pten$^{+/-}$ female mice may be modified by haploinsufficiency for Slc6a4, as happens with brain size, we examined 8-week-old female wild type, Pten haploinsufficient, Slc6a4 haploinsufficient and Pten$^{+/-}$; Slc6a4$^{+/-}$ compound mutant mice. Slc6a4 haploinsufficient and Pten$^{+/-}$; Slc6a4$^{+/-}$ mice responded normally in a test of olfactory habituation-dishabituation (FIG. 6), indicating no gross impairment of olfaction in these mice. We found that Slc6a4 haploinsufficient mice displayed a decreased preference for interacting with a stimulus mouse in the social approach assay as compared to wild type mice, although this did not fall below the threshold for significance. However, Pten$^{+/-}$; Slc6a4$^{+/-}$ mice, did not show a significant preference for interacting with a stimulus mouse (FIG. 3A). Analyzing these data using a social approach-avoidance score (28) (time in social chamber 1 minus time in non-social chamber 3), we found that the time spent interacting with a stimulus mouse was significantly less in Pten$^{+/-}$; Slc6a4$^{+/-}$ mice than in wild type, Pten haploinsufficient, or Slc6a4 haploinsufficient mice (FIG. 3B). This result is consistent with haploinsufficiency for Pten and Slc6a4 acting additively to influence an ASD-relevant behavioral phenotype, social approach.

Figure 3C:
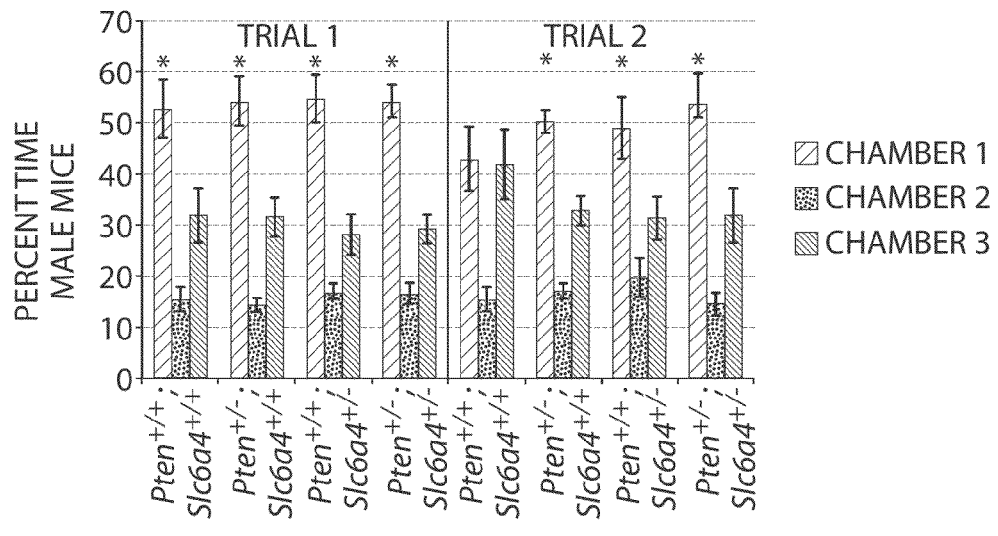
Figure 3D:
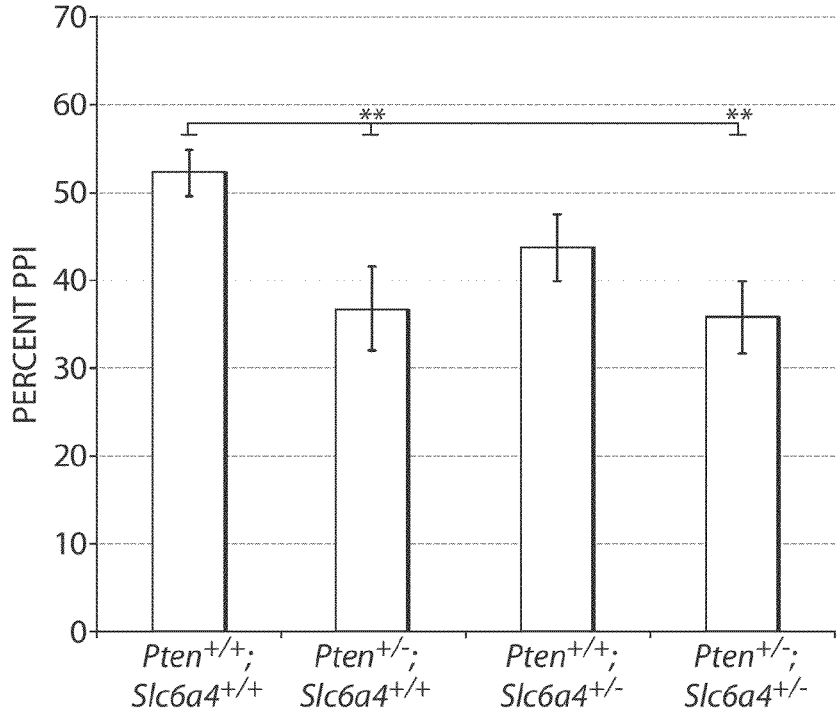

To examine further social approach in Pten$^{+/-}$ male mice, we tested 8-week old male wild type, Pten haploinsufficient, Slc6a4 haploinsufficient and Pten$^{+/-}$; Slc6a4$^{+/-}$ mice for social approach and recognition behavior. To do this, we adapted our three chamber apparatus to a protocol used to test social recognition in Oxytocin knockout mice, which show normal initial social investigation behavior but fail to recognize the same social target upon re-exposure after 30 minutes (30-32). Consistent with our findings for 12-week-old male wild type and Pten haploinsufficient mice (FIG. 2C), we did not observe a significant change in preference for social interaction in any of these genotypes in the male groups for the first 10-minute trial (trial 1) (FIG. 3C). Upon re-exposure to the same social target in trial 2 (5 minutes), wild type mice showed equal interest in investigating the control and stimulus mouse-containing chambers, with this effect presumably due to habituation (FIG. 3C). In contrast, Pten haploinsufficient, Slc6a4 haploinsufficient and Pten$^{+/-}$; Slc6a4$^{+/-}$ mice did not show attenuation of preference for social investigation between the first and second trials (FIG. 3D). This finding indicates that haploinsufficiency for Pten and Slc6a4 may impair social recognition in male mice; however, further testing will be necessary to separate out a specific deficit in the social recognition pathway (i.e. Oxytocin-Vasopressin-Dopamine) versus sustained interest in social interaction.

In tests of prepulse inhibition, the relationship between Pten and Slc6a4 haploinsufficiency appeared to be epistatically dominant rather than additive, with Pten haploinsufficient and Pten$^{+/-}$; Slc6a4$^{+/-}$ mice each being significantly impaired as compared to wild type but not as compared to one another (FIG. 3D). This suggests that interactions between Pten and Slc6a4 may have a degree of specificity as regards the development of brain circuitry underlying behavior. We speculate that cooperative function of Pten and Slc6a4 is particularly important for the assembly and function of circuitry involved in social behavior, as it is for brain size control, but not necessarily for circuitry involved in other ASD-relevant behaviors such as sensorimotor gating.

Figure 4A:
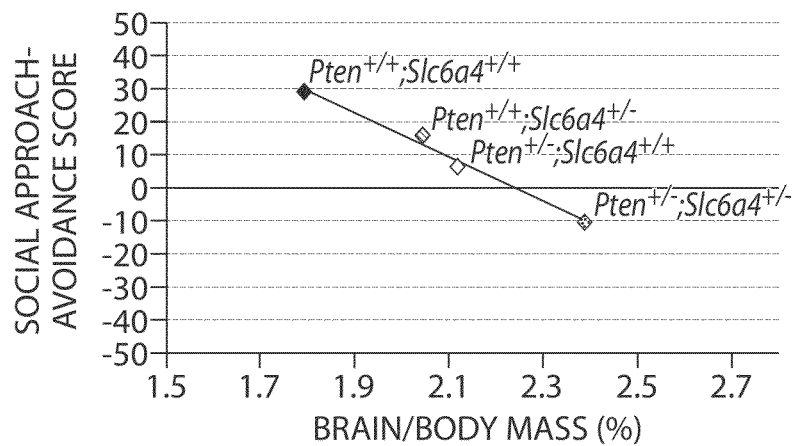
FIG. 4: Correlation between brain mass and sociability across and within genotypes FIG. 4(A) Plot of population means for brain mass (normalized to body mass) (X-axis) and social approach-avoidance scores (Y-axis) for 8 week old female Pten$^{+/+}$; Slc6a4$^{+/+}$ (n=7), Pten$^{+/-}$; Slc6a4$^{+/+}$ (n=8), Pten$^{+/+}$; Slc6a4$^{+/-}$ (n=10) and Pten$^{+/-}$; Slc6a4$^{+/-}$ (n=11) mice. r=−0.98. * * * (B through E) Individual subjects from panel (A), arranged by genotype, plotted for brain mass (normalized to body mass) (X-axis) and social approach-avoidance scores (Y-axis).
FIG. 4(B) Pten$^{+/+}$; Slc6a4$^{+/+}$: r=0.77; P<0.05 (r to P conversion).
FIG. 4(C) Pten$^{+/-}$; Slc6a4$^{+/+}$: r=0.70; P<0.05
FIG. 4(D) Pten$^{+/+}$; Slc6a4$^{+/-}$: r=0.60; P=0.07
FIG. 4(E) Pten$^{+/-}$; Slc6a4$^{+/-}$: r=0.65; P<0.05
Figure 4B:
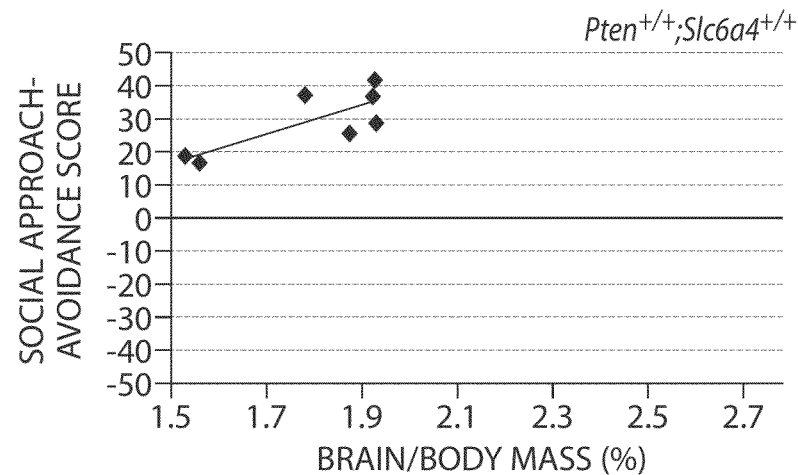
Figure 4C:
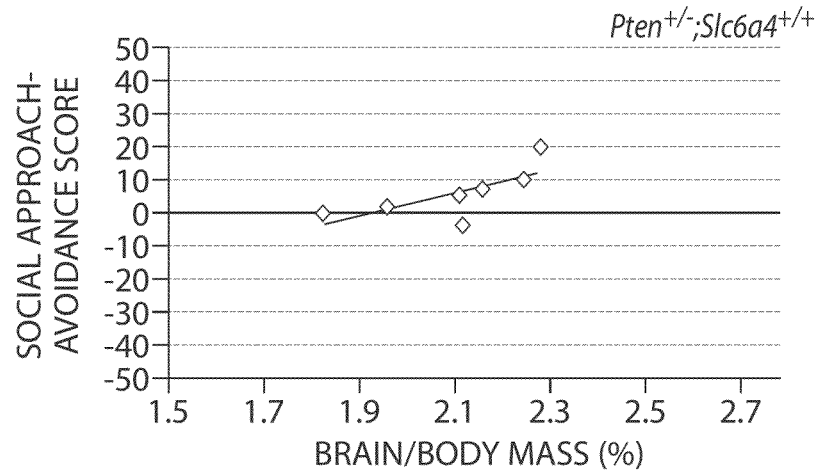
Figure 4D:
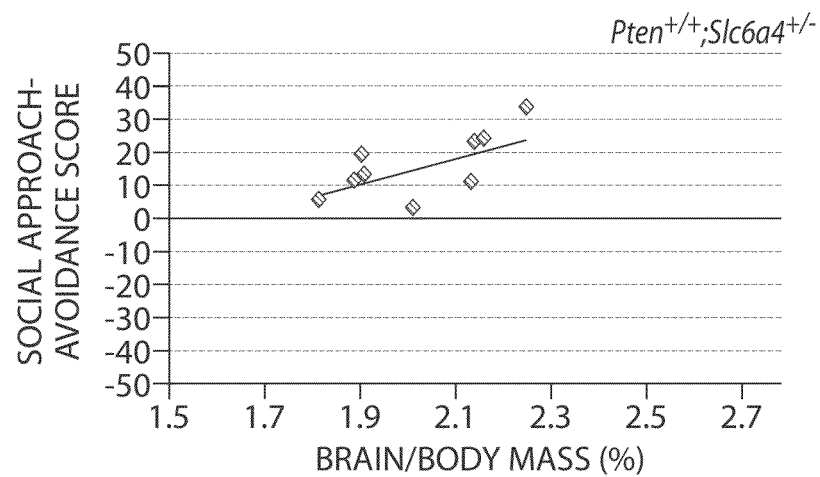
Figure 4E:
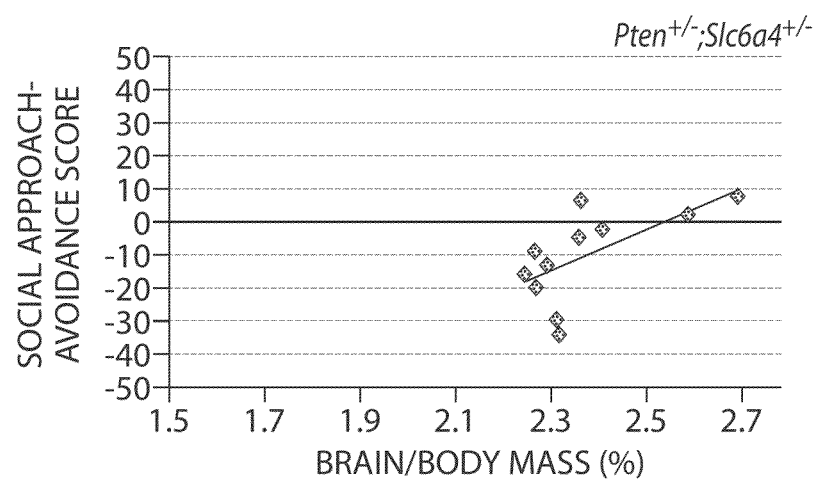

We next asked whether the social approach phenotype related to brain size across genotypes and within each genotype. Analyzing population means revealed a negative correlation between brain size (relative to body mass) and social approach-avoidance score across genotypes (FIG. 4A). Surprisingly, analysis of individual subjects within each genotype showed a significant positive correlation between these measures in each group, with the possible exception of Slc6a4 haploinsufficient mice which showed more variability (FIG. 4B through E). This indicates that haploinsufficiency for Pten and Slc6a4 leads to a decrease in sociability with increase in brain size. Within each of these genotypes, however, intragroup factors appear to mediate an increase in sociability with increase in brain size.

Mechanisms by which serotonin signaling (including Slc6a4) and the PI3K pathway (including Pten) may interact to influence brain development are illustrated in FIG. 7. One possibility is that Pten and Serotonin receptor may physically interact in a regulatory manner to influence brain development. In neurons, Pten binds 5-HT2c receptor and, via its phosphatase activity, limits agonist-induced activation of this receptor and modulates the firing rate of dopaminergic neurons in the ventral tegmediate area (10). We have run a preliminary test of the effects of a specific antagonist of 5-HT2c receptor, SB 242084 (33), on social approach behavior in female Pten haploinsufficient mice and found that this drug can offset deficits in social approach behavior (FIG. 5). It is interesting to note that three drugs that have been reported as alleviating symptoms of autism—the atypical antipsychotics risperidone (34) and olanzapine (35), and the antidepressant fluoxetine (36)—all have antagonistic effects on the 5-HT2c receptor, in addition to well-known effects targeting other members of the serotonin and dopamine pathways. Based on our findings reported here, we propose that antagonism of the 5-HT2c receptor may be relevant for the action of these drugs in autism.

Discussion

As regards brain structure and function, we find that Pten haploinsufficient mice of both genders have brain overgrowth and that females have deficits in social approach behavior. We find that these phenotypes can be modified in an additive fashion by Slc6a4 haploinsufficiency. These findings are striking given that autism affects males over females at a ratio of approximately 4:1. At present we do not know why we see differential effects of gender in social behavior in Pten haploinsufficient mice. It is important to emphasize that the social approach assay we have used captures only one aspect of social behavior in rodents that may be relevant to ASD. Further testing of behaviors such as ultrasonic vocalization or social reward will be necessary to fully characterize the extent and nature of social impairment in these mice; it is possible that such tests may yet reveal deficits in male Pten haploinsufficient mice. However, one interesting possible clue for these gender differences in our assays comes from reports of evidence for a link between immune system dysfunction, particularly autoimmunity, and ASD (19, 37, 38). Postmortem studies have also shown an increase in the expression of several markers for neuroinflammation in ASD (39). Importantly, Pten$^{+/-}$ mice have immune system abnormalities, including autoimmunity, and these effects are more pronounced in female mice as compared to male mice (40). This argues that Pten haploinsufficient mice will be a useful model to study the influence of gender and immune system dysfunction on neural development.

We propose that modulation of the serotonin receptor 5-HT2cR is a potential therapeutic target for ASD. In addition to SB 24208, several other drugs have been developed which act to antagonize 5-HT2cR with more specificity than risperidone (34), olanzapine (35) and fluoxetine (36); we predict that these may also be useful as therapeutics for ASD. Examples of such drugs include FR 260010 (41) and RS 102221 (42). In addition to acting on serotonin receptor 5-HT2cR, it is also possible that the PI3K/Akt pathway is directly modulated by serotonin signaling. In cultured rodent hippocampal neurons, addition of 5-HT$_{1A}$ receptor agonist can activate Akt and this activation can be blocked via pharmacological inhibition of PI3K (43). 5-HT$_{1A}$ receptor is expressed in the brain as early as mid-embryogenesis (44), suggesting that altered activity of this receptor could modify the course of brain development even from early stages of morphogenesis. Stimulation of 5-HT$_{1B}$ receptor is also capable of activating Akt (45). There is evidence that this receptor modulates axonal responses to guidance cues in the developing neocortex (46) and that excess serotonin acting on this receptor is responsible for specific cytoarchitechtonic abnormalities in Slc6a4 knockout mice (47). Either mechanism could converge on molecules capable of influencing morphogenesis, growth and neuronal function, including mTOR, GSK-3beta, Creb, and NF-kappa-B. Interestingly, serotonergic stimulation increases (48), and serotonin deficiency decreases (49), levels of GSK-3beta phosphorylated at Ser 9 in the mouse brain. Regulation of GSK-3beta at Ser 9 by Pten via Akt is involved in establishing and maintaining neuronal polarity (50), and levels of phospho-GSK-3beta are reported as elevated in the brains of mice in which Pten has been conditionally knocked out in the CNS (21). While further experiments will be necessary to verify this model, molecules upon which the serotonin and Pten-PI3K pathways converge may prove useful biomarkers, as well as therapeutic targets, for a subset of individuals with ASD.

Our data also suggest that a negative correlation exists between brain size and sociability across the genotypes examined in the present study. However, at the level of individual animals within a given genotypic group, we find a significant positive correlation between brain size and sociability. We interpret this finding as indicating that, in reference to sociability, there are both beneficial and detrimental ways of changing brain size. We have identified haploinsufficiency for Pten and Slc6a4 as additively leading to correlated increases in brain size and decreased sociability. Perhaps acting secondary to this, and possibly reflecting environmental effects on neural plasticity, we speculate that specific pathways influence brain size in a beneficial manner in reference to sociability. While in autism, clinical data indicate a negative correlation between head circumference and sociability (18, 19), evidence exists from numerous studies that a positive correlation exists between brain size and social complexity in primates and other animals (reviewed in (51)). The possibility that distinct biological pathways influence brain size and lead to differential outcomes as regards sociability may help explain this paradox. We hypothesize that these pathways may act as evolutionary substrates for changes in social behavior within and across species.

Our results also argue that overall brain size may serve as a convenient phenotypic readout for screening for interactions with the serotonin and PI3K pathways. Future work will be aimed at characterizing the mechanisms underlying anatomical and behavioral phenotypes reported here and how genetic, environmental and pharmacological manipulations impact these phenotypes. It will be interesting to examine whether proposed mechanisms of ASD pathophysiology, including increased excitation/inhibition ratios (52) and altered local versus long-distance connectivity in frontal cortex (53) is apparent in this model. An elevated rate of de novo genomic copy number variation has been observed in ASD (54). Given that Pten has a role in the maintenance of genomic stability and that a loss of Pten results in an accumulation of double-stranded DNA breaks (55, 56), it is possible that a background of PTEN haploinsufficiency may increase the probability of a secondary modifying event, such as a copy number variation in a gene relevant to ASD, occurring. As regards environmental modifiers, polychlorinated biphenyls (PCBs) are a class of organic compounds capable of disrupting neocortical development and are candidates for interacting with genetic susceptibility in ASD etiology (57). Experimental evidence exists for a PCB, PCB77, altering nitric oxide signaling and NF-kappa-B activity via the PI3K pathway, and this effect can be offset by inhibiting PI3K (58). Given the role of PTEN as a negative regulator of PI3K signaling, we hypothesize that haploinsufficiency for PTEN may be a genetic risk factor for ASD susceptibility in response to exposure to environmental toxins that impinge on the PI3K pathway, such as PCBs.

REFERENCES

1. Cully, M., You, H., Levine, A. J., & Mak, T. W. (2006) Beyond PTEN mutations: the PI3K pathway as an integrator of multiple inputs during tumorigenesis. Nat Rev Cancer 6, 184-192.
2. Butler, M. G., et al. (2005) Subset of individuals with autism spectrum disorders and extreme macrocephaly associated with germline PTEN tumour suppressor gene mutations. J Med Genet 42, 318-321.
3. Goffin, A., Hoefsloot, L. H., Bosgoed, E., Swillen, A., & Fryns, J. P. (2001) PTEN mutation in a family with Cowden syndrome and autism. Am J Med Genet 105, 521-524.
4. Herman, G. E., et al. (2007) Increasing knowledge of PTEN germline mutations: Two additional patients with autism and macrocephaly. Am J Med Genet A 143, 589-593.
5. Herman, G. E., et al. (2007) Genetic testing in autism: how much is enough? Genet Med 9, 268-274.
6. Bartlett, C. W., Gharani, N., Millonig, J. H., & Brzustowicz, L. M. (2005) Three autism candidate genes: a synthesis of human genetic analysis with other disciplines. Int J Dev Neurosci 23, 221-234.
7. Hessl, D., et al. (2007) Brief Report: Aggression and Stereotypic Behavior in Males with Fragile X Syndrome-Moderating Secondary Genes in a "Single Gene" Disorder. J Autism Dev Disord.
8. Wassink, T. H., et al. (2007) Cerebral cortical gray matter overgrowth and functional variation of the serotonin transporter gene in autism. Arch Gen Psychiatry 64, 709-717.
9. Brune, C. W., et al. (2006) 5-HTTLPR Genotype-Specific Phenotype in Children and Adolescents With Autism. Am J Psychiatry 163, 2148-2156.
10. Ji, S. P., et al. (2006) Disruption of PTEN coupling with 5-HT2C receptors suppresses behavioral responses induced by drugs of abuse. Nat Med 12, 324-329.
11. Cowen, D. S. (2007) Serotonin and neuronal growth factors—a convergence of signaling pathways. J Neurochem 101, 1161-1171.
12. Eng, C. (2003) PTEN: one gene, many syndromes. Hum Mutat 22, 183-198.
13. Podsypanina, K., et al. (1999) Mutation of Pten/Mmac1 in mice causes neoplasia in multiple organ systems. Proc Natl Acad Sci U S A 96, 1563-1568.
14. Muhle, R., Trentacoste, S. V., & Rapin, I. (2004) The genetics of autism. Pediatrics 113, e472-486.
15. Marui, T., et al. (2004) Association between the neurofibromatosis-1 (NF1) locus and autism in the Japanese population. Am J Med Genet B Neuropsychiatr Genet 131, 43-47.
16. Mbarek, O., et al. (1999) Association study of the NF1 gene and autistic disorder. Am J Med Genet 88, 729-732.
17. Courchesne, E. & Pierce, K. (2005) Brain overgrowth in autism during a critical time in development: implications for frontal pyramidal neuron and interneuron development and connectivity. Int J Dev Neurosci 23, 153-170.
18. Courchesne, E., Carper, R., & Akshoomoff, N. (2003) Evidence of brain overgrowth in the first year of life in autism. Jama 290, 337-344.
19. Sacco, R., et al. (2007) Clinical, morphological, and biochemical correlates of head circumference in autism. Biol Psychiatry 62, 1038-1047.
20. Backman, S. A., et al. (2001) Deletion of Pten in mouse brain causes seizures, ataxia and defects in soma size resembling Lhermitte-Duclos disease. Nat Genet 29, 396-403.
21. Kwon, C. H., et al. (2006) Pten regulates neuronal arborization and social interaction in mice. Neuron 50, 377-388.
22. Kwon, C. H., et al. (2001) Pten regulates neuronal soma size: a mouse model of Lhermitte-Duclos disease. Nat Genet 29, 404-411.
23. Bengel, D., et al. (1998) Altered brain serotonin homeostasis and locomotor insensitivity to 3,4-methylene- 24. Crawley, J. N. (2004) Designing mouse behavioral tasks relevant to autistic-like behaviors. Ment Retard Dev Disabil Res Rev 10, 248-258.
25. Frankland, P. W., et al. (2004) Sensorimotor gating abnormalities in young males with fragile X syndrome and Fmrl-knockout mice. Mol Psychiatry 9, 417-425.
26. McAlonan, G. M., et al. (2002) Brain anatomy and sensorimotor gating in Asperger's syndrome. Brain 125, 1594-1606.
27. Perry, W., Minassian, A., Lopez, B., Maron, L., & Lincoln, A. (2007) Sensorimotor gating deficits in adults with autism. Biol Psychiatry 61, 482-486.
28. Brodkin, E. S., Hagemann, A., Nemetski, S. M., & Silver, L. M. (2004) Social approach-avoidance behavior of inbred mouse strains towards DBA/2 mice. Brain Res 1002, 151-157.
29. Nadler, J. J., et al. (2004) Automated apparatus for quantitation of social approach behaviors in mice. Genes Brain Behav 3, 303-314.
30. Crawley, J. N., et al. (2007) Social approach behaviors in oxytocin knockout mice: comparison of two independent lines tested in different laboratory environments. Neuropeptides 41, 145-163.
31. Ferguson, J. N., Aldag, J. M., Insel, T. R., & Young, L. J. (2001) Oxytocin in the medial amygdala is essential for social recognition in the mouse. J Neurosci 21, 8278-8285.
32. Ferguson, J. N., et al. (2000) Social amnesia in mice lacking the oxytocin gene. Nat Genet 25, 284-288.
33. Kennett, G. A., et al. (1997) SB 242084, a selective and brain penetrant 5-HT2C receptor antagonist. Neuropharmacology 36, 609-620.
34. McCracken, J. T., et al. (2002) Risperidone in children with autism and serious behavioral problems. N Engl J Med 347, 314-321.
35. Malone, R. P., Cater, J., Sheikh, R. M., Choudhury, M. S., & Delaney, M. A. (2001) Olanzapine versus haloperidol in children with autistic disorder: an open pilot study. J Am Acad Child Adolesc Psychiatry 40, 887-894.
36. Cook, E. H., Jr., Rowlett, R., Jaselskis, C., & Leventhal, B. L. (1992) Fluoxetine treatment of children and adults with autistic disorder and mental retardation. J Am Acad Child Adolesc Psychiatry 31, 739-745.
37. Cabanlit, M., Wills, S., Goines, P., Ashwood, P., & Van de Water, J. (2007) Brain-specific autoantibodies in the plasma of subjects with autistic spectrum disorder. Ann N Y Acad Sci 1107, 92-103.
38. Sweeten, T. L., Bowyer, S. L., Posey, D. J., Halberstadt, G. M., & McDougle, C. J. (2003) Increased prevalence of familial autoimmunity in probands with pervasive developmental disorders. Pediatrics 112, e420.
39. Vargas, D. L., Nascimbene, C., Krishnan, C., Zimmerman, A. W., & Pardo, C. A. (2005) Neuroglial activation and neuroinflammation in the brain of patients with autism. Ann Neurol 57, 67-81.
40. Di Cristofano, A., et al. (1999) Impaired Fas response and autoimmunity in Pten+/- mice. Science 285, 2122-2125.
41. Harada, K., et al. (2006) Anxiolytic activity of a novel potent serotonin 5-HT2C receptor antagonist FR260010: a comparison with diazepam and buspirone. Eur J Pharmacol 553, 171-184.
42. Bonhaus, D. W., et al. (1997) RS-102221: a novel high affinity and selective, 5-HT2C receptor antagonist. Neuropharmacology 36, 621-629.
43. Cowen, D. S., Johnson-Farley, N. N., & Travkina, T. (2005) 5-HT receptors couple to activation of Akt, but not extracellular-regulated kinase (ERK), in cultured hippocampal neurons. J Neurochem 93, 910-917.
44. Bonnin, A., Peng, W., Hewlett, W., & Levitt, P. (2006) Expression mapping of 5-HT1 serotonin receptor subtypes during fetal and early postnatal mouse forebrain development. Neuroscience 141, 781-794.
45. Hsu, E. H., Lochan, A. C., & Cowen, D. S. (2001) Activation of Aka by human 5-hydroxytryptamine (serotonin) 1B receptors is sensitive to inhibitors of MEK. J Pharmacol Exp Ther 298, 825-832.
46. Bonnin, A., Torii, M., Wang, L., Rakic, P., & Levitt, P. (2007) Serotonin modulates the response of embryonic thalamocortical axons to netrin-1. Nat Neurosci 10, 588-597.
47. Salichon, N., et al. (2001) Excessive activation of serotonin (5-HT) 1B receptors disrupts the formation of sensory maps in monoamine oxidase a and 5-ht transporter knock-out mice. J Neurosci 21, 884-896.
48. Li, X., et al. (2004) In vivo regulation of glycogen synthase kinase-3beta (GSK3beta) by serotonergic activity in mouse brain. Neuropsychopharmacology 29, 1426-1431.
49. Beaulieu, J. M., et al. (2008) Role of GSK3 beta in behavioral abnormalities induced by serotonin deficiency. Proc Natl Acad Sci U S A 105, 1333-1338.
50. Jiang, H., Guo, W., Liang, X., & Rao, Y. (2005) Both the establishment and the maintenance of neuronal polarity require active mechanisms: critical roles of GSK-3beta and its upstream regulators. Cell 120, 123-135.
51. Dunbar, R. I. & Shultz, S. (2007) Evolution in the social brain. Science 317, 1344-1347.
52. Rubenstein, J. L. & Merzenich, M. M. (2003) Model of autism: increased ratio of excitation/inhibition in key neural systems. Genes Brain Behav 2, 255-267.
53. Courchesne, E. & Pierce, K. (2005) Why the frontal cortex in autism might be talking only to itself: local over-connectivity but long-distance disconnection. Curr Opin Neurobiol 15, 225-230.
54. Sebat, J., et al. (2007) Strong association of de novo copy number mutations with autism. Science 316, 445-449.
55. Puc, J. & Parsons, R. (2005) PTEN loss inhibits CHK1 to cause double stranded-DNA breaks in cells. Cell Cycle 4, 927-929.
56. Shen, W. H., et al. (2007) Essential role for nuclear PTEN in maintaining chromosomal integrity. Cell 128, 157-170.
57. Kenet, T., Froemke, R. C., Schreiner, C. E., Pessah, I. N., & Merzenich, M. M. (2007) Perinatal exposure to a non-coplanar polychlorinated biphenyl alters tonotopy, receptive fields, and plasticity in rat primary auditory cortex. Proc Natl Acad Sci U S A 104, 7646-7651.
58. Lim, E. J., Smart, E. J., Toborek, M., & Hennig, B. (2007) The role of caveolin-1 in PCB77-induced eNOS phosphorylation in human-derived endothelial cells. Am J Physiol Heart Circ Physiol 293, H3340-3347.
59. Luo, A. H., et al. (2002) Impaired olfactory behavior in mice deficient in the alpha subunit of G(o). Brain Res 941, 62-71.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

The entire contents of all of the references (including literature references, issued patents, published patent applications), or relevant portions thereof, cited throughout this application are hereby expressly incorporated by reference for the purpose cited herein.

The invention claimed is:

1. A method for treating an autism spectrum disorder comprising
administering to a subject in need of such treatment one or more therapeutic molecules that is an antagonist or inhibitor of the 5-HT2c receptor signaling pathway, wherein the antagonist or inhibitor of 5-HT2c receptor signaling pathway is SB242084 and wherein the said subject has a PTEN deficiency and/or SLC6A4 deficiency and/or increased circulating serotonin.

2. The method of claim 1, wherein the dose of SB 242084 administered is about 0.1-1 mg/kg/day.

3. The method of claim 2, wherein the dose of SB 242084 administered is about 1-10 mg/kg/day.

4. The method of claim 1, wherein the subject is a human.

5. The method of claim 1, wherein the antagonist or inhibitor of the 5-HT2c receptor signaling pathway is administered orally, intravenously, intramuscularly, intranasally, intraperitoneally, subcutaneously, or intrathecally.

6. The method of claim 1, wherein the antagonist or inhibitor of the 5-HT2c receptor signaling pathway is administered after diagnosis of the autism spectrum disorder.

7. The method of claim 1, wherein the antagonist or inhibitor of the 5-HT2c receptor signaling pathway is administered prophylactically before diagnosis of the autism spectrum disorder.

8. The method of claim 1, wherein the subject has or is believed to have ASD, but is free of symptoms other than ASD symptoms that would call for treatment with the antagonist or inhibitor of the 5-HT2c receptor signaling pathway.

9. The method of claim 1, further comprising testing the subject for PTEN deficiency and/or SLC6A4 deficiency and/or increased circulating serotonin.

10. The method of claim 1, further comprising testing the subject for macrocephaly (brain overgrowth) and/or deficits in social behavior, such as a deficit in social interaction and/or a deficit in social memory.

11. The method of claim 10, wherein the antagonist or inhibitor of the 5-HT2c receptor signaling pathway is administered to the subject only if macrocephaly and/or deficits in social behavior are detected by the testing.

* * * * *